US012577600B2

(12) United States Patent　　　　　　(10) Patent No.: US 12,577,600 B2
Strack-Logue et al.　　　　　　　　　　(45) Date of Patent: Mar. 17, 2026

(54) MODIFICATION OF RNA-RELATED ENZYMES FOR ENHANCED PRODUCTION

(71) Applicant: Translate Bio, Inc., Lexington, MA (US)

(72) Inventors: Bettina Strack-Logue, Lexington, MA (US); Frank DeRosa, Lexington, MA (US); Michael Heartlein, Lexington, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 0 days.

(21) Appl. No.: 18/481,401

(22) Filed: Oct. 5, 2023

(65) Prior Publication Data

US 2024/0175065 A1　　May 30, 2024

Related U.S. Application Data

(63) Continuation of application No. 17/217,752, filed on Mar. 30, 2021, now abandoned, which is a continuation of application No. 16/165,372, filed on Oct. 19, 2018, now Pat. No. 10,995,354, which is a continuation of application No. 15/294,249, filed on Oct. 14, 2016, now Pat. No. 10,144,942.

(60) Provisional application No. 62/241,350, filed on Oct. 14, 2015.

(51) Int. Cl.
　　*C12N 9/12*　　　(2006.01)
　　*C07K 14/47*　　　(2006.01)
　　*C12N 15/62*　　　(2006.01)
　　*C12P 19/34*　　　(2006.01)

(52) U.S. Cl.
　　CPC .............. *C12P 19/34* (2013.01); *C07K 14/47* (2013.01); *C12N 9/1241* (2013.01); *C12N 15/62* (2013.01); *C12Y 207/0705* (2013.01); *C07K 2319/35* (2013.01); *C07K 2319/95* (2013.01)

(58) Field of Classification Search
None
See application file for complete search history.

(56) References Cited

U.S. PATENT DOCUMENTS

| | | | |
|---|---|---|---|
| 5,705,385 A | 1/1998 | Bally et al. |
| 5,976,567 A | 11/1999 | Wheeler |
| 5,981,501 A | 11/1999 | Wheeler et al. |
| 6,534,484 B1 | 3/2003 | Wheeler et al. |
| 6,815,432 B2 | 11/2004 | Wheeler et al. |
| 7,422,902 B1 | 9/2008 | Wheeler et al. |
| 7,655,413 B2 | 2/2010 | Butt et al. |
| 7,745,651 B2 | 6/2010 | Heyes et al. |
| 7,799,565 B2 | 9/2010 | Maclachlan et al. |
| 7,803,397 B2 | 9/2010 | Heyes et al. |
| 7,901,708 B2 | 3/2011 | Maclachlan et al. |
| 8,101,741 B2 | 1/2012 | Maclachlan et al. |
| 8,119,369 B2 | 2/2012 | Zuo et al. |
| 8,188,263 B2 | 5/2012 | Maclachlan et al. |
| 8,236,943 B2 | 8/2012 | Lee et al. |
| 8,329,070 B2 | 12/2012 | Maclachlan et al. |
| 8,513,403 B2 | 8/2013 | Maclachlan et al. |
| 8,569,256 B2 | 10/2013 | Heyes et al. |
| 8,710,200 B2 | 4/2014 | Schrum et al. |
| 8,822,663 B2 | 9/2014 | Schrum et al. |
| 8,853,377 B2 | 10/2014 | Guild et al. |
| 8,883,202 B2 | 11/2014 | Manoharan et al. |
| 8,936,942 B2 | 1/2015 | Heyes et al. |
| 8,980,864 B2 | 3/2015 | Hoge et al. |
| 8,999,351 B2 | 4/2015 | Manoharan et al. |
| 8,999,950 B2 | 4/2015 | Maclachlan et al. |
| 9,018,187 B2 | 4/2015 | Heyes et al. |
| 9,051,567 B2 | 6/2015 | Fitzgerald et al. |
| 9,061,059 B2 | 6/2015 | Chakraborty et al. |
| 9,074,208 B2 | 7/2015 | Maclachlan et al. |
| 9,089,604 B2 | 7/2015 | Chakraborty et al. |
| 9,095,552 B2 | 8/2015 | Chakraborty et al. |
| 9,107,886 B2 | 8/2015 | Chakraborty et al. |
| 9,114,113 B2 | 8/2015 | Chakraborty et al. |
| 9,181,319 B2 | 11/2015 | Schrum et al. |
| 9,186,325 B2 | 11/2015 | Manoharan et al. |
| 9,186,372 B2 | 11/2015 | de Fougerolles et al. |
| 9,187,748 B2 | 11/2015 | Geisbert et al. |
| 9,192,651 B2 | 11/2015 | Chakraborty et al. |
| 9,220,755 B2 | 12/2015 | Chakraborty et al. |
| 9,220,792 B2 | 12/2015 | Chakraborty et al. |
| 9,233,141 B2 | 1/2016 | Chakraborty et al. |
| 9,254,311 B2 | 2/2016 | Bancel et al. |
| 9,295,689 B2 | 3/2016 | de Fouaerolles et al. |

(Continued)

FOREIGN PATENT DOCUMENTS

| | | |
|---|---|---|
| CA | 2807552 | 9/2012 |
| EP | 1519714 | 10/2010 |

(Continued)

OTHER PUBLICATIONS

U.S. Appl. No. 15/294,249 2017/0159093 U.S. Pat. No. 10,144,942, filed Oct. 14, 2016 Jun. 8, 2017 Dec. 4, 2018, Bettina Strack-Logue, Modification of RNA-Related Enzymes for Enhanced Production.
U.S. Appl. No. 16/165,372 2019/0136283 U.S. Pat. No. 10,995,354, filed Oct. 19, 2018 May 8, 2019 May 4, 2021, Bettina Strack-Logue, Modification of RNA-Related Enzymes for Enhanced Production.
U.S. Appl. No. 17/217,752 2022/0010347, filed Mar. 30, 2021 Jan. 13, 2022, Bettina Strack-Logue, Modification of RNA-Related Enzymes for Enhanced Production.

(Continued)

*Primary Examiner* — Richard G Hutson

(74) *Attorney, Agent, or Firm* — LATHROP GPM LLP; James H. Velema, Esq.

(57)　　　　　ABSTRACT

The present invention provides, among other things, methods and compositions for large-scale production of capped mRNA using SUMO-Guanylyl Transferase fusion protein.

4 Claims, 2 Drawing Sheets

Specification includes a Sequence Listing.

(56)  References Cited

U.S. PATENT DOCUMENTS

| | | | |
|---|---|---|---|
| 9,301,993 | B2 | 4/2016 | Chakraborty et al. |
| 9,303,079 | B2 | 4/2016 | Chakraborty et al. |
| 9,334,328 | B2 | 5/2016 | Schrum et al. |
| 9,345,780 | B2 | 5/2016 | Manoharan et al. |
| 9,352,042 | B2 | 5/2016 | Heyes et al. |
| 9,352,048 | B2 | 5/2016 | Manoharan et al. |
| 9,364,435 | B2 | 6/2016 | Yaworski et al. |
| 9,394,234 | B2 | 7/2016 | Chen et al. |
| 9,404,127 | B2 | 8/2016 | Yaworski et al. |
| 9,428,751 | B2 | 8/2016 | MacDonald et al. |
| 9,464,124 | B2 | 10/2016 | Bancel et al. |
| 10,144,942 | B2 | 12/2018 | Strack-Logue et al. |
| 10,995,354 | B2 | 5/2021 | Strack-Logue et al. |
| 2002/0192651 | A1 | 12/2002 | Wheeler et al. |
| 2003/0181410 | A1 | 9/2003 | Wheeler et al. |
| 2004/0142025 | A1 | 7/2004 | Maclachlan et al. |
| 2006/0008910 | A1 | 1/2006 | Maclachlan et al. |
| 2006/0083780 | A1 | 4/2006 | Heyes et al. |
| 2007/0135372 | A1 | 6/2007 | Maclachlan et al. |
| 2009/0270481 | A1 | 10/2009 | Maclachlan et al. |
| 2010/0041152 | A1 | 2/2010 | Wheeler et al. |
| 2011/0256175 | A1 | 10/2011 | Hope et al. |
| 2011/0311583 | A1 | 12/2011 | Manoharan et al. |
| 2012/0065252 | A1 | 3/2012 | Schrum et al. |
| 2012/0128760 | A1 | 5/2012 | Manoharan et al. |
| 2012/0142756 | A1 | 6/2012 | Guild et al. |
| 2012/0202871 | A1 | 8/2012 | Heyes et al. |
| 2012/0237975 | A1 | 9/2012 | Schrum et al. |
| 2012/0251618 | A1 | 10/2012 | Schrum et al. |
| 2012/0328668 | A1 | 12/2012 | Maclachlan et al. |
| 2013/0195967 | A1 | 8/2013 | Guild et al. |
| 2013/0237594 | A1 | 9/2013 | de Fouaerolles et al. |
| 2013/0259923 | A1 | 10/2013 | Bancel et al. |
| 2013/0259924 | A1 | 10/2013 | Bancel et al. |
| 2013/0266640 | A1 | 10/2013 | de Fougerolles et al. |
| 2014/0010861 | A1 | 1/2014 | Bancel et al. |
| 2014/0044772 | A1 | 2/2014 | Maclachlan et al. |
| 2014/0105964 | A1 | 4/2014 | Bancel et al. |
| 2014/0105965 | A1 | 4/2014 | Bancel et al. |
| 2014/0147432 | A1 | 5/2014 | Bancel et al. |
| 2014/0147454 | A1 | 5/2014 | Chakraborty et al. |
| 2014/0148502 | A1 | 5/2014 | Bancel et al. |
| 2014/0155472 | A1 | 6/2014 | Bancel et al. |
| 2014/0155473 | A1 | 6/2014 | Bancel et al. |
| 2014/0155474 | A1 | 6/2014 | Bancel et al. |
| 2014/0155475 | A1 | 6/2014 | Bancel et al. |
| 2014/0171485 | A1 | 6/2014 | Bancel et al. |
| 2014/0179756 | A1 | 6/2014 | Maclachlan et al. |
| 2014/0179771 | A1 | 6/2014 | Bancel et al. |
| 2014/0186432 | A1 | 7/2014 | Bancel et al. |
| 2014/0193482 | A1 | 7/2014 | Bancel et al. |
| 2014/0194494 | A1 | 7/2014 | Bancel et al. |
| 2014/0199371 | A1 | 7/2014 | Bancel et al. |
| 2014/0200261 | A1 | 7/2014 | Hoae et al. |
| 2014/0200262 | A1 | 7/2014 | Bancel et al. |
| 2014/0200263 | A1 | 7/2014 | Bancel et al. |
| 2014/0200264 | A1 | 7/2014 | Bancel et al. |
| 2014/0206752 | A1 | 7/2014 | Afevan et al. |
| 2014/0206753 | A1 | 7/2014 | Guild et al. |
| 2014/0206755 | A1 | 7/2014 | Bancel et al. |
| 2014/0206852 | A1 | 7/2014 | Hoqe et al. |
| 2014/0221465 | A1 | 8/2014 | Bancel et al. |
| 2014/0243399 | A1 | 8/2014 | Schrum et al. |
| 2014/0249208 | A1 | 9/2014 | Bancel et al. |
| 2014/0255467 | A1 | 9/2014 | Bancel et al. |
| 2014/0255468 | A1 | 9/2014 | Bancel et al. |
| 2014/0275227 | A1 | 9/2014 | Hoqe et al. |
| 2014/0275229 | A1 | 9/2014 | Bancel et al. |
| 2014/0294937 | A1 | 10/2014 | Maclachlan et al. |
| 2014/0343129 | A1 | 11/2014 | de Fougerolles et al. |
| 2015/0005372 | A1 | 1/2015 | Hoqe et al. |
| 2015/0017211 | A1 | 1/2015 | de Fougerolles et al. |
| 2015/0044277 | A1 | 2/2015 | Bancel et al. |
| 2015/0050354 | A1 | 2/2015 | Bouchon et al. |
| 2015/0051268 | A1 | 2/2015 | Bancel et al. |
| 2015/0056253 | A1 | 2/2015 | Bancel et al. |
| 2015/0064235 | A1 | 3/2015 | Bancel et al. |
| 2015/0064236 | A1 | 3/2015 | Bancel et al. |
| 2015/0064242 | A1 | 3/2015 | Heyes et al. |
| 2015/0064725 | A1 | 3/2015 | Schrum et al. |
| 2015/0086614 | A1 | 3/2015 | Bancel et al. |
| 2015/0111248 | A1 | 4/2015 | Bancel et al. |
| 2015/0111945 | A1 | 4/2015 | Geisbert et al. |
| 2015/0166465 | A1 | 6/2015 | Chen et al. |
| 2015/0190515 | A1 | 7/2015 | Manoharan et al. |
| 2015/0265708 | A1 | 9/2015 | Manoharan et al. |
| 2015/0315541 | A1 | 11/2015 | Bancel et al. |
| 2015/0315584 | A1 | 11/2015 | MacDonald et al. |
| 2015/0366997 | A1 | 12/2015 | Guild et al. |
| 2016/0095924 | A1 | 4/2016 | Hooe et al. |
| 2016/0114011 | A1 | 4/2016 | Bancel et al. |
| 2016/0115477 | A1 | 4/2016 | Maclachlan et al. |
| 2016/0115483 | A1 | 4/2016 | Maclachlan et al. |
| 2016/0136236 | A1 | 5/2016 | Hoge et al. |
| 2016/0151284 | A1 | 6/2016 | Heyes et al. |
| 2016/0158385 | A1 | 6/2016 | Bancel et al. |
| 2016/0193299 | A1 | 7/2016 | de Fougerolles et al. |
| 2016/0194368 | A1 | 7/2016 | Hoqe et al. |
| 2016/0194625 | A1 | 7/2016 | Hoqe et al. |
| 2016/0199485 | A1 | 7/2016 | Manoharan et al. |
| 2016/0213785 | A1 | 7/2016 | Manoharan et al. |
| 2016/0237108 | A1 | 8/2016 | Fraley et al. |
| 2016/0237134 | A1 | 8/2016 | Hoqe et al. |
| 2016/0250354 | A1 | 9/2016 | Manoharan et al. |
| 2016/0251681 | A1 | 9/2016 | Yaworski et al. |
| 2016/0256567 | A1 | 9/2016 | Heyes et al. |
| 2016/0256568 | A1 | 9/2016 | Heves et al. |
| 2016/0264971 | A1 | 9/2016 | Geisbert et al. |
| 2016/0274089 | A1 | 9/2016 | Ciufolini et al. |
| 2016/0304552 | A1 | 10/2016 | Roy et al. |
| 2016/0317647 | A1 | 11/2016 | Ciaramella et al. |
| 2016/0317676 | A1 | 11/2016 | Hope et al. |
| 2017/0159093 | A1 | 6/2017 | Strack-Logue et al. |
| 2019/0136283 | A1 | 5/2019 | Strack-Logue et al. |
| 2022/0010347 | A1 | 1/2022 | Strack-Logue et al. |

FOREIGN PATENT DOCUMENTS

| | | | | |
|---|---|---|---|---|
| EP | | 2449106 | 5/2012 | |
| EP | | 2338478 | 6/2013 | |
| EP | | 2823809 | 1/2015 | |
| WO | WO 2002/090495 | | 11/2002 | |
| WO | WO 2005/026372 | | 3/2005 | |
| WO | WO 2005/121348 | | 12/2005 | |
| WO | WO-2006073976 A2 * | | 7/2006 | ........... C07K 14/395 |
| WO | WO 2009/127060 | | 10/2006 | |
| WO | WO 2008/083271 | | 7/2008 | |
| WO | WO 2010/042877 | | 4/2010 | |
| WO | WO 2011/141705 | | 11/2011 | |
| WO | WO 2012/135805 | | 11/2011 | |
| WO | WO 2012/019168 | | 2/2012 | |
| WO | WO 2012/170930 | | 12/2012 | |
| WO | WO 2013/039857 | | 3/2013 | |
| WO | WO 2013/039861 | | 3/2013 | |
| WO | WO 2013/090186 | | 6/2013 | |
| WO | WO 2013/101690 | | 7/2013 | |
| WO | WO 2013/126803 | | 8/2013 | |
| WO | WO 2013/130161 | | 9/2013 | |
| WO | WO 2013/151663 | | 10/2013 | |
| WO | WO 2013/151664 | | 10/2013 | |
| WO | WO 2013/151666 | | 10/2013 | |
| WO | WO 2013/151667 | | 10/2013 | |
| WO | WO 2013/151668 | | 10/2013 | |
| WO | WO 2013/151670 | | 10/2013 | |
| WO | WO 2013/151671 | | 10/2013 | |
| WO | WO 2013/151672 | | 10/2013 | |
| WO | WO 2013/151736 | | 10/2013 | |
| WO | WO 2014/028429 | | 2/2014 | |
| WO | WO 2014/089486 | | 6/2014 | |
| WO | WO 2014/113089 | | 7/2014 | |
| WO | WO 2014/144039 | | 9/2014 | |

(56)     References Cited

FOREIGN PATENT DOCUMENTS

| | | |
|---|---|---|
| WO | WO 2014/144711 | 9/2014 |
| WO | WO 2014/144767 | 9/2014 |
| WO | WO 2014/152027 | 9/2014 |
| WO | WO 2014/152030 | 9/2014 |
| WO | WO 2014/152031 | 9/2014 |
| WO | WO 2014/152211 | 9/2014 |
| WO | WO 2014/152540 | 9/2014 |
| WO | WO 2014/158795 | 10/2014 |
| WO | WO 2014/159813 | 10/2014 |
| WO | WO 2015/006747 | 1/2015 |
| WO | WO 2015/048744 | 4/2015 |
| WO | WO 2015/051169 | 4/2015 |
| WO | WO 2015/051173 | 4/2015 |
| WO | WO 2015/058069 | 4/2015 |
| WO | WO 2015/085142 | 6/2015 |
| WO | WO 2015/085318 | 6/2015 |
| WO | WO 2015/089511 | 6/2015 |
| WO | WO 2015/011633 | 1/2016 |
| WO | WO 2016/054421 | 4/2016 |
| WO | WO 2016/071857 | 5/2016 |
| WO | WO 2016/077123 | 5/2016 |
| WO | WO 2016/077125 | 5/2016 |
| WO | WO 2016/118724 | 7/2016 |
| WO | WO 2016/118725 | 7/2016 |
| WO | WO 2016/154127 | 9/2016 |
| WO | WO 2016/164762 | 10/2016 |
| WO | WO-2016193226 A1 * | 12/2016 ............. C12N 11/02 |

OTHER PUBLICATIONS

U.S. Appl. No. 18/481,401, filed Oct. 5, 2023, Bettina Strack-Logue, Modification of RNA-Related Enzymes for Enhanced Production.

Anonymous, SUMOpro-3 Gene Fusion Technology—Product Manual, Jan. 28, 2014, pp. 1-10.

Fresco et al., Active Site of the mRNA-Capping Enzyme Guanylyltransferase From *Saccharomyces cerevisiae*: Similarity to the Nucleotidyl Attachment Motif of DNA and RNA Ligases, Proceedings of the National Academy of Science, National Academy of Sciences, US, vol. 91, Jul. 1, 1994, pp. 6624-6628.

Guo et al., Interaction and Mutual Stabilization of the Two Subunits of Vaccinia Virus D mNRA Capping Enzyme Coexpressed in *Escherichia coli*, Proceedings of the National Academy of Sciences, National Academy of Sciences, US, vol. 87, No. 11, Jun. 1, 1990, pp. 4023-4027.

Ho et al., "A Yeast-Based Genetic System for Functional Analysis of Viral mRNA Cappina Enzymes", Journal of Viroloav, 2000, vol. 74, No. 12, pp. 5486-5494.

International Report on Patentability for PCT International Patent Application No. PCT/US2016/057044, dated Apr. 17, 2018.

International Search Report and Written Opinion for PCT International Patent Application No. PCT/US2016/057044, dated Apr. 20, 2017.

Kyrieleis et al., Crystal Structure of Vaccinia Virus mRNA Capping Enzyme Provides Insights into the Mechanism and Evolution of the Capping Apparatus, vol. 22, No. 3, Mar. 4, 2014, pp. 452-456.

Tsukamoto et al., Cloning and Characterization of Two Human cDNAs Encoding the mRNA Capping Enzyme, Biochemical and Biophysical Research Communications, 1998, vol. 243, pp. 101-108.

* cited by examiner

FIG. 1A

Cap 0 mRNA

FIG. 1B

Cap 1 mRNA

MODIFICATION OF RNA-RELATED ENZYMES FOR ENHANCED PRODUCTION

RELATED APPLICATIONS

This application is a continuation of U.S. patent application Ser. No. 17/217,752, filed Mar. 30, 2021, which is a continuation of U.S. patent application Ser. No. 16/165,372, filed Oct. 19, 2018, now U.S. Pat. No. 10,995,354, which is a continuation of U.S. patent application Ser. No. 15/294, 249, filed Oct. 14, 2016, now U.S. Pat. No. 10,144,942, which claims priority to U.S. Provisional Patent Application Ser. No. 62/241,350, filed Oct. 14, 2015, the entire disclosures of which are hereby incorporated herein by reference.

SEQUENCE LISTING

The instant application contains a Sequence Listing which has been submitted electronically in XML format and is hereby incorporated by reference in its entirety. Said XML file, created on Oct. 5, 2023, is named 746819_SA9-846CON3_ST26. xml and is 19,787 bytes in size.

BACKGROUND

Messenger RNA ("mRNA") therapy is becoming an increasingly important approach for the treatment of a variety of diseases. Effective mRNA therapy requires effective delivery of the mRNA to the patient and efficient production of the protein encoded by the mRNA within the patient's body. To optimize mRNA delivery and protein production in vivo, a proper cap are typically required at the 5' end of the construct, which protects the mRNA from degradation and facilitates successful protein translation. Therefore, the large-scale production of enzymes capable of capping mRNA is particularly important for producing mRNA for therapeutic applications.

SUMMARY OF THE INVENTION

The present invention provides improved methods for effective production of enzymes capable of capping mRNA. The present invention is, in part, based on the surprising discovery that modifying a guanylyl transferase (GT) with a SUMO tag makes it possible to produce GT on the large scale needed for producing capped mRNA for therapeutic applications.

Thus, in one aspect, the present invention provides methods of producing a capped RNA or RNA analog oligonucleotide, wherein a fusion protein facilitates the steps of transferring and methylating a guanylyl molecule to the 5' end of the RNA or RNA analog oligonucleotide.

In some embodiments, the fusion protein comprises a guanylyl transferase and a small ubiquitin-like molecule (SUMO) protein. In some embodiments, the guanylyl transferase comprises SEQ ID NO: 6 and SEQ ID NO: 7 and the SUMO protein comprises SEQ ID NO: 1. In some embodiments, the fusion protein comprises SEQ ID NO: 8 and SEQ ID NO: 7.

In some embodiments, the one end of the RNA or RNA analog oligonucleotide is the 5' end.

In some embodiments, the fusion protein has comparable phosphatase activity, guanylyl transferase activity and methylation activity relative to a wild-type guanylyl transferase protein.

In another aspect, the present invention provides fusion proteins, wherein a fusion protein comprises guanylyl transferase and a small ubiquitin-like molecule (SUMO) protein.

In some embodiments, the guanylyl transferase comprises SEQ ID NO: 6 and SEQ ID NO: 7 and the SUMO protein comprises SEQ ID NO: 1. In some embodiments, the guanylyl transferase comprises a large subunit and a small subunit. In some embodiments, the SUMO protein is covalently linked and co-expressed with the large subunit. In some embodiments, the fusion protein has comparable phosphatase activity, guanylyl transferase activity and methylation activity relative to a wild-type guanylyl transferase protein.

In another aspect, the present invention provides vectors encoding a fusion protein comprising guanylyl transferase protein and a small ubiquitin-like molecule (SUMO) protein.

In some embodiments, the vector comprises SEQ ID NO: 5 and SEQ ID NO: 2. In some embodiments, the vector comprises SEQ ID NO: 5, SEQ ID NO: 2, and SEQ ID NO: 3. In some embodiments, the vector comprises SEQ ID NO: 4 and SEQ ID NO: 3.

In another aspect, the present invention provides methods to produce a guanylyl transferase by fermentation, comprising: a) culturing in a fermentation medium a microorganism that is transformed with at least one recombinant nucleic acid molecule comprising a nucleic acid sequence encoding a guanylyl transferase that has an amino acid sequence that is at least 90% identical SEQ ID NO: 6 and SEQ ID NO: 7; and b) collecting a product produced from the step of culturing.

In some embodiments, the guanylyl transferase comprises a guanylyl transferase fusion protein. In some embodiments, the guanylyl transferase fusion protein has comparable phosphatase activity, guanylyl transferase activity and methylation activity relative to a wild-type guanylyl transferase protein. In some embodiments, the guanylyl transferase fusion protein comprises a small ubiquitin-like molecule (SUMO) protein. In some embodiments, the guanylyl transferase fusion protein comprises SEQ ID NO: 8.

In some embodiments, the SUMO protein is bound to the guanylyl transferase by a covalent link. In some embodiments, the covalent link is between the SUMO protein and a large subunit of the guanylyl transferase.

In some embodiments, the fermentation medium is selected from the group consisting of Terrific Broth, Cinnabar, 2×YT and LB. In some embodiments, the microorganism is a bacterium.

In some embodiments, the nucleic acid sequence encoding the guanylyl transferase is at least 90% identical to SEQ ID NO: 2 and SEQ ID NO: 3.

In some embodiments, the recombinant nucleic acid molecule further comprises a nucleic acid sequence encoding a small ubiquitin-like molecule (SUMO) protein. In some embodiments, the nucleic acid sequence encoding a small ubiquitin-like molecule (SUMO) protein is at least 90% identical to SEQ ID NO: 5.

In some embodiments, the product is a guanylyl transferase. In some embodiments, the product is a guanylyl transferase comprises a guanylyl transferase fusion protein. In some embodiments, the guanylyl transferase fusion protein further comprises a small ubiquitin-like molecule (SUMO) protein.

BRIEF DESCRIPTION OF THE DRAWING

The drawings are for illustration purposes and are in no way limiting.

FIGS. 1A and 1B are diagrams of exemplary mRNA capped structures present in various embodiments of the invention.

DEFINITIONS

Figure 2:
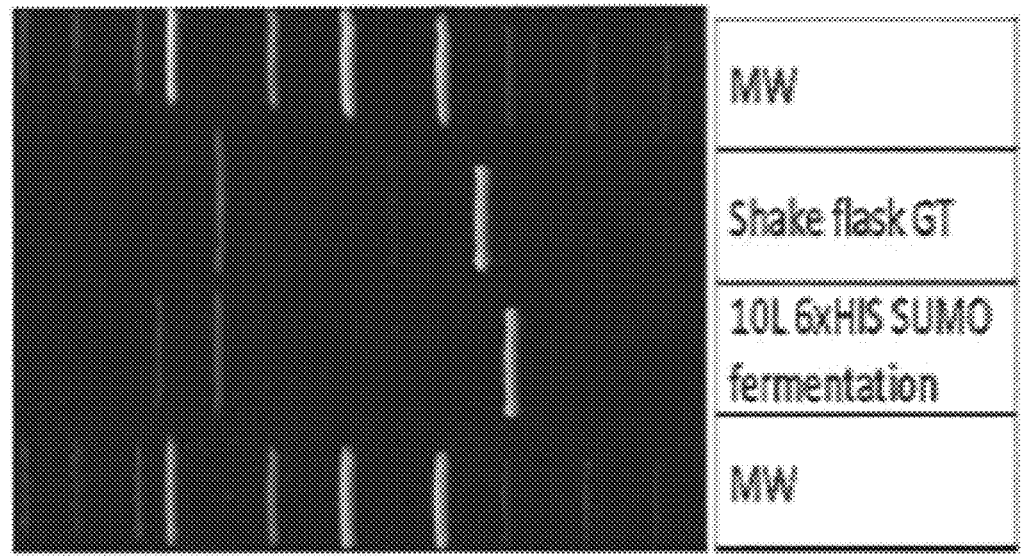
FIG. 2 demonstrates exemplary yield of soluble SUMO-GT protein produced by fermentation compared to that of GT protein produced via the shake flask method.

In order for the present invention to be more readily understood, certain terms are first defined. Additional definitions for the following terms and other terms are set forth throughout the specification.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Batch culture: As used herein, the term "batch culture" refers to a method of culturing cells in which all the components that will ultimately be used in culturing the cells, including the medium (see definition of "medium" below) as well as the cells themselves, are provided at the beginning of the culturing process. Thus, a batch culture typically refers to a culture allowed to progress from inoculation to conclusion without refeeding the cultured cells with fresh medium. A batch culture is typically stopped at some point and the cells and/or components in the medium are harvested and optionally purified.

Biologically active: As used herein, the phrase "biologically active" refers to a characteristic of any substance that has activity in a biological system (e.g., cell culture, organism, etc.). For instance, a substance that, when administered to an organism, has a biological effect on that organism, is considered to be biologically active. Biological activity can also be determined by in vitro assays (for example, in vitro enzymatic assays such as sulfate release assays). In particular embodiments, where a protein or polypeptide is biologically active, a portion of that protein or polypeptide that shares at least one biological activity of the protein or polypeptide is typically referred to as a "biologically active" portion. In some embodiments, a protein is produced and/or purified from a cell culture system, which displays biologically activity when administered to a subject. In some embodiments, a protein requires further processing in order to become biologically active. In some embodiments, a protein requires posttranslational modification such as, but is not limited to, glycosylation (e.g., sialyation), farnysylation, cleavage, folding, formylglycine conversion and combinations thereof, in order to become biologically active. In some embodiments, a protein produced as a proform (i.e. immature form), may require additional modification to become biologically active.

Bioreactor: As used herein, the term "bioreactor" refers to a vessel used for the growth of a host cell culture. A bioreactor can be of any size so long as it is useful for the culturing of mammalian cells. Typically, a bioreactor will be at least 1 liter and may be 10, 100, 250, 500, 1000, 2500, 5000, 8000, 10,000, 12,0000 liters or more, or any volume in between. Internal conditions of a bioreactor, including, but not limited to pH, osmolarity, $CO_2$ saturation, $O_2$ saturation, temperature and combinations thereof, are typically controlled during the culturing period. A bioreactor can be composed of any material that suitable for holding cells in media under the culture conditions of the present invention, including glass, plastic or metal. In some embodiments, a bioreactor may be used for performing animal cell culture. In some embodiments, a bioreactor may be used for performing mammalian cell culture. In some embodiments, a bioreactor may be used with cells and/or cell lines derived from such organisms as, but not limited to, mammalian cell, insect cells, bacterial cells, yeast cells and human cells. In some embodiments, a bioreactor is used for large-scale cell culture production and is typically at least 100 liters and may be 200, 500, 1000, 2500, 5000, 8000, 10,000, 12,0000 liters or more, or any volume in between. One of ordinary skill in the art will be aware of and will be able to choose suitable bioreactors for use in practicing the present invention.

Cell density: As used herein, the term "cell density" refers to that number of cells present in a given volume of medium.

Cell culture or culture: As used herein, these terms refer to a cell population that is gown in a medium under conditions suitable to survival and/or growth of the cell population. As will be clear to those of ordinary skill in the art, these terms as used herein may refer to the combination comprising the cell population and the medium in which the population is grown.

Cultivation: As used herein, the term "cultivation" or grammatical equivalents refers to a process of maintaining cells under conditions favoring growth or survival. The terms "cultivation" and "cell culture" or any synonyms are used inter-changeably in this application.

Culture vessel: As used herein, the term "culture vessel" refers to any container that can provide an aseptic environment for culturing cells. Exemplary culture vessels include, but are not limited to, glass, plastic, or metal containers.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Fed-batch culture: As used herein, the term "fed-batch culture" refers to a method of culturing cells in which additional components are provided to the culture at some time subsequent to the beginning of the culture process. The provided components typically comprise nutritional supplements for the cells which have been depleted during the culturing process. A fed-batch culture is typically stopped at some point and the cells and/or components in the medium are harvested and optionally purified.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g., between nucleic acid molecules (e.g., DNA molecules and/ or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Various other sequence alignment programs are available and can be used to determine sequence identity such as, for example, Clustal.

Integrated Viable Cell Density: As used herein, the term "integrated viable cell density" refers to the average density of viable cells over the course of the culture multiplied by the amount of time the culture has run. Assuming the amount of polypeptide and/or protein produced is proportional to the number of viable cells present over the course of the culture, integrated viable cell density is a useful tool for estimating the amount of polypeptide and/or protein produced over the course of the culture.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.)

Medium: As used herein, the term "medium" refer to a solution containing nutrients which nourish growing cells. Typically, these solutions provide essential and non-essential amino acids, vitamins, energy sources, lipids, and trace elements required by the cell for minimal growth and/or survival. The solution may also contain components that enhance growth and/or survival above the minimal rate, including hormones and growth factors. In some embodiments, medium is formulated to a pH and salt concentration optimal for cell survival and proliferation. In some embodiments, medium may be a "chemically defined medium"—a serum-free media that contains no proteins, hydrolysates or components of unknown composition. In some embodiment, chemically defined medium is free of animal-derived components and all components within the medium have a known chemical structure. In some embodiments, medium may be a "serum based medium"—a medium that has been supplemented with animal derived components such as, but not limited to, fetal calf serum, horse serum, goat serum, donkey serum and/or combinations thereof.

Nucleic acid: As used herein, the term "nucleic acid," in its broadest sense, refers to a compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Perfusion process: As used herein, the term "perfusion process" refers to a method of culturing cells in which additional components are provided continuously or semi-continuously to the culture subsequent to the beginning of the culture process. The provided components typically comprise nutritional supplements for the cells which have been depleted during the culturing process. A portion of the cells and/or components in the medium are typically harvested on a continuous or semi-continuous basis and are optionally purified. Typically, a cell culture process involving a perfusion process is referred to as "perfusion culture." Typically, nutritional supplements are provided in a fresh medium during a perfusion process. In some embodiments, a fresh medium may be identical or similar to the base medium used in the cell culture process. In some embodiments, a fresh medium may be different than the base medium but containing desired nutritional supplements. In some embodiments, a fresh medium is a chemically-defined medium.

Seeding: As used herein, the term "seeding" refers to the process of providing a cell culture to a bioreactor or another vessel for large scale cell culture production. In some embodiments a "seed culture" is used, in which the cells have been propagated in a smaller cell culture vessel, i.e. Tissue-culture flask, Tissue-culture plate, Tissue-culture roller bottle, etc., prior to seeding. Alternatively, in some embodiments, the cells may have been frozen and thawed Viable cell density: As used herein, the term "viable cell density" refers to the number of living cells per unit volume.

DETAILED DESCRIPTION

The present invention provides, among other things, methods and compositions for large-scale production of capped mRNA using SUMO- Guanylyl Transferase fusion protein.

Various aspects of the invention are described in further detail in the following subsections. The use of subsections is not meant to limit the invention. Each subsection may apply to any aspect of the invention. In this application, the use of "or" means "and/or" unless stated otherwise.

SUMO-Guanylyl Transferase Fusion Protein

Small Ubiquitin-like Modifier (SUMO)

As used herein, a SUMO tag is any protein or a portion of a protein that can substitute for at least partial activity of a SUMO protein.

SUMO proteins are small proteins that are covalently attached to and detached from other proteins in order to modify the functions of those proteins. The modification of a protein with a SUMO protein is a post-translational modification involved in various cellular processes such as nuclear-cytosolic transport, transcriptional regulation, apoptosis, protein stability, response to stress and progression through the cell cycle. There are at least 4 SUMO paralogs in vertebrates, designated SUMO-1, SUMO-2, SUMO-3, and SUMO-4. SUMO-2 and SUMO-3 are structurally and functionally very similar and are distinct from SUMO-1. The amino acid sequence (SEQ ID NO: 1) spans amino acids 3-92 of a typical wild-type or naturally occurring SUMO-3 protein is shown in Table 1. In addition, a codon optimized DNA sequence encoding the SUMO-3 protein is also provided in Table 1, as SEQ ID NO: 5.

TABLE 1

| Small Ubiquitin-like Modifier | |
| --- | --- |
| SUMO-3 Protein sequence | EEKPKEGVKTENDHINLKVAGQDGSVVQFKIKRHTPLSKLMKAY CERQGLSMRQIRFRFDGQPINETDTPAQLEMEDEDTIDVFQQQTGG (SEQ ID NO: 1) |
| SUMO-3 DNA sequence | GAAGAGAAACCGAAAGAGGGCGTTAAGACCGAGAATGACCAC ATTAACCTGAAGGTCGCTGGTCAAGATGGCAGCGTGGTGCAGT TTAAGATCAAGCGTCACACGCCGTTGAGCAAGCTGATGAAGGC TTACTGCGAGCGTCAGGGTCTGAGCATGCGTCAGATCCGCTTTC GTTTCGATGGCCAGCCGATCAATGAGACTGACACCCCAGCGCA ACTGG (SEQ ID NO: 5) | immediately prior to providing them to the bioreactor or vessel. The term refers to any number of cells, including a single cell.

Subject: As used herein, the term "subject" means any mammal, including humans. In certain embodiments of the present invention the subject is an adult, an adolescent or an infant. Also contemplated by the present invention are the administration of the pharmaceutical compositions and/or performance of the methods of treatment in-utero.

Vector: As used herein, "vector" refers to a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

Thus, in some embodiments, a SUMO protein is a human SUMO-3 protein (SEQ ID NO: 1). In some embodiments, the SUMO protein may be another SUMO paralog, such as SUMO-1, SUMO-2 or SUMO-4. In some embodiments, a suitable replacement protein may be a homologue or an analogue of human SUMO-3 protein. For example, a homologue or an analogue of SUMO-3 protein may be a modified SUMO-3 protein containing one or more amino acid substitutions, deletions, and/or insertions as compared to a wild-type or naturally-occurring SUMO-3 protein (e.g. SEQ ID NO: 1), while retaining substantial SUMO-3 protein activity. Thus, in some embodiments, an enzyme suitable for the present invention is substantially homologous to a wild-type or naturally-occurring SUMO-3 protein (SEQ ID NO: 1). In some embodiments, an enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 1. In some embodiments, an enzyme suitable for the present invention is substantially identical to a wild-type or naturally-occurring SUMO-3 protein (SEQ ID NO: 1). In some embodiments, a protein suitable for the present invention contains a fragment or a portion of a SUMO protein. In some embodiments, the SUMO protein comprises human SUMO-1, human SUMO-2, human SUMO-3, any one of *Arabidopsis Zhalania* SUMO-1 through SUMO-8, tomato SUMO, any one of *Xenopus laevis* SUMO-1 through SUMO-3, *Drosophila melanogasler* Smt3, *Caenorhabdilis elegans* SMO-1, *Schizosaccharomyces pombe* Pmt3, malarial parasite *Plasmodium falciparum* SUMO, mold *Aspergillus nidulans* SUMO, an equivalent thereof, a homologue thereof, or a combination thereof.

In some embodiments, the SUMO protein is encoded by a nucleic acid derived from an organism selected from the group consisting of human, mouse, insect, plant, yeast, and other eukaryotic organisms. In some embodiments, the SUMO protein is encoded by a nucleic acid derived from an organism selected from the group consisting of *Homo sapiens, Arabidopsis Zhalania*, tomato, *Xenopus laevis, Drosophila melanogasler, Caenorhabdilis elegans, Schizosaccharomyces pombe, Plasmo diumfalciparum*, or *Aspergillus nidulans*. In some embodiments, a nucleic acid suitable for the present invention has an sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 5. In some embodiments, a nucleic acid suitable for the present invention is substantially identical to a nucleic acid encoding a wild-type or naturally-occurring SUMO-3 protein (SEQ ID NO: 5).

Guanylyl Transferase (GT)

As used herein, a GT protein is any protein or portion of a protein that can substitute for at least partial activity of naturally-occurring Guanylyl Transferase (GT) protein. As used herein, the terms "a GT protein" and "a GT enzyme" and grammatical equivalents are used interchangeably.

GT is an enzyme derived from the Vaccinia Virus system that facilitates the transfer and methylation of a guanylyl molecule to the 5' end of a messenger RNA molecule. This process, known as mRNA capping, is highly regulated and important for the creation of stable and mature mRNA able to undergo translation during protein synthesis. The GT enzyme comprises a heterodimer that includes a "large subunit" (D1, about 97 kDa) and a "small subunit (D12, about 33 kDa). GT provides three enzymatic functions: phosphatase activity (cleavage of the nascent 5' triphosphate of mRNA to a diphosphate), guanylyl transferase activity (incorporation of a GTP molecule to the 5' end of the mRNA moiety) and methylation activity (incorporation of a methyl group at the N7 position of the guanylyl base). The amino acid sequence of the large subunit (SEQ ID NO: 6) and small subunit (SEQ ID NO: 7) of a typical wild-type or naturally occurring GT protein are shown in Table 2. In addition, codon optimized DNA sequences encoding the large and small subunits of GT are also provided in Table 2, as SEQ ID NO: 2 and SEQ ID NO: 3, respectively.

TABLE 2

| Guanylyl Transferase | |
|---|---|
| Large subunit (Protein sequence) | MDANVVSSSTIATYIDALAKNASELEQRSTAYEINNELELVFIKPPL ITLTNVVNISTIQESFIRFTVTNKEGVKIRTKIPLSKVHGLDVKNVQL VDAIDNIVWEKKSLVTENRLHKECLLRLSTEERHIFLDYKKYGSSI RLELVNLIQAKTKNFTIDFKLKYFLGSGAQSKSSLLHAINHPKSRPN TSLEIEFTPRDNETVPYDELIKELTTLSRHIFMASPENVILSPPINAPI KTFMLPKQDIVGLDLENLYAVTKTDGIPITIRVTSNGLYCYFTHLG YIIRYPVKRIIDSEVVVFGEAVKDKNWTVYLIKLIEPVNAINDRLEE SKYVESKLVDICDRIVFKSKKYEGPFTTTSEVVDMLSTYLPKQPEG VILFYSKGPKSNIDFKIKKENTIDQTANVVFRYMSSEPIIFGESSIFVE YKKFSNDKGFPKEYGSGKIVLYNGVNYLNNIYCLEYINTHNEVGI KSVVVPIKFIAEFLVNGEILKPRIDKTMKYINSEDYYGNQHNIIVEH LRDQSIKIGDIFNEDKLSDVGHQYANNDKFRLNPEVSYFTNKRTRG PLGILSNYVKTLLISMYCSKTFLDDSNKRKVLAIDFGNGADLEKYF YGEIALLVATDPDADAIARGNERYNKLNSGIKTKYYKFDYIQETIR SDTFVSSVREVFYFGKFNIIDWQFAIHYSFHPRHYATVMNNLSELT ASGGKVLITTMDGDKLSKLTDKKTFIIHKNLPSSENYMSVEKIADD RIVVYNPSTMSTPMTEYIIKKNDIVRVFNEYGFVLVDNVDFATIIER SKKFINGASTMEDRPSTRNFFELNRGAIKCEGLDVEDLLSYYVVY VFSKR (SEQ ID NO: 6) |
| Small subunit (Protein sequence) | MDEIVKNIREGTHVLLPFYETLPELNLSLGKSPLPSLEYGANYFLQI SRVNDLNRMPTDMLKLFTHDIMLPESDLDKVYEILKINSVKYYGR STKADAVVADLSARNKLFKRERDAIKSNNHLTENNLYISDYKMLT FDVFRPLFDFVNEKYCIIKLPTLFGRGVIDTMRIYCSLFKNVRLLKC VSDSWLKDSAIMVASDVCKKNLDLFMSHVKSVTKSSSWKDVNSV QFSILNNPVDTEFINKFLEFSNRVYEALYYVHSLLYSSMTSDSKSIE NKHQRRLVKLLL (SEQ ID NO: 7) |
| Large subunit (DNA sequence) | AGATGGAAGATGAAGATACCATCGACGTCTTTCAGCAACAGAC CGGTGGTATGGATGCTAACGTCGTTAGCAGCAGCACCATTGCG ACTTACATTGATGCACTGGCCAAAAACGCATCTGAGCTTGAGC AGCGCAGCACCGCCTACGAGATCAATAACGAATTGGAGCTGGT TTTCATTAAACCGCCGCTGATCACGCTGACGAACGTCGTGAAC ATTAGCACGATTCAAGAGAGCTTTATTCGTTTCACCGTTACCAA TAAAGAAGGCGTGAAGATCCGTACCAAGATTCCGCTGAGCAAA GTGCATGGTCTGGACGTGAAAAATGTGCAGCTGGTTGATGCGA TCGATAACATCGTGTGGGAGAAGAAATCTTTGGTCACGGAAAA TCGTCTGCACAAGGAATGTCTGCTGCGTCTGTCAACCGAAGAA CGCCACATCTTCCTGGACTACAAGAAGTATGGTTCCAGCATCCG TCTGGAACTGGTGAACCTGATTCAGGCAAAGACCAAGAACTTC ACCATTGACTTCAAACTGAAGTATTTCCTGGGCTCTGGTGCACA |

TABLE 2-continued

Guanylyl Transferase

```
                        GAGCAAATCCAGCTTGTTGCACGCGATTAACCATCCGAAGAGC
                        CGTCCGAATACGAGCCTGGAGATCGAATTCACGCCGCGTGATA
                        ACGAAACCGTTCCGTACGATGAGCTGATTAAAGAACTGACGAC
                        GTTGAGCCGCCACATCTTTATGGCCAGCCCGGAAAACGTGATC
                        CTTAGCCCGCCTATCAATGCGCCGATTAAAACCTTTATGTTACC
                        GAAACAAGACATTGTGGGTCTGGACCTGGAAAACCTGTACGCG
                        GTCACCAAAACGGACGGCATTCCGATCACGATTCGTGTTACCA
                        GCAATGGTCTGTACTGCTATTTCACTCATTTGGGCTATATCATT
                        CGTTATCCGGTGAAACGCATCATTGATTCTGAGGTTGTCGTTTT
                        CGGCGAAGCAGTCAAGGACAAGAATTGGACTGTGTACCTGATC
                        AAATTGATTGAACCGGTTAACGCCATCAATGACCGCCTGGAAG
                        AGTCGAAATATGTTGAAAGCAAACTGGTGGATATTTGTGATCG
                        TATCGTGTTCAAGAGCAAGAAATATGAAGGCCCGTTCACCACG
                        ACCAGCGAAGTTGTTGACATGCTGAGCACCTATCTGCCGAAAC
                        AACCTGAGGGTGTGATTCTGTTTTACTCCAAGGGTCCGAAGAG
                        CAACATTGATTTCAAAATCAAGAAAGAGAATACCATTGATCAG
                        ACCGCCAACGTTGTGTTCCGCTATATGTCCAGCGAGCCTATCAT
                        TTTCGGTGAGTCGAGCATCTTTGTTGAATACAAAAAGTTTAGCA
                        ACGATAAGGGTTTTCCGAAAGAATACGGTTCCGGTAAGATTGT
                        GTTGTACAACGGCGTCAATTATCTGAACAACATCTACTGTCTGG
                        AGTACATCAATACCCATAACGAAGTTGGCATTAAGTCTGTTGTC
                        GTCCCGATCAAATTCATCGCGGAGTTCCTGGTTAACGGTGAGAT
                        TCTGAAGCCGCGTATTGATAAAACTATGAAATACATTAACTCC
                        GAAGATTACTACGGTAATCAGCATAACATCATCGTCGAGCACT
                        TGCGTGATCAAAGCATTAAGATCGGTGACATCTTTAACGAAGA
                        TAAGCTGAGCGATGTAGGCCACCAGTATGCGAACAATGACAAA
                        TTTCGCCTGAATCCGGAAGTCAGCTACTTTACGAATAAGCGCAC
                        CCGTGGTCCACTGGGTATCCTGAGCAATTATGTTAAAACCCTGT
                        TGATTTCCATGTACTGCTCCAAAACGTTCCTGGACGACAGCAAC
                        AAGCGCAAAGTTCTGGCGATCGACTTCGGTAATGGTGCCGATC
                        TGGAGAAGTACTTTTATGGTGAGATCGCATTGCTGGTTGCTACC
                        GACCCGGATGCAGATGCGATCGCCCGTGGCAACGAGCGTTACA
                        ATAAGCTGAATAGCGGTATCAAGACCAAATACTACAAATTCGA
                        CTATATTCAAGAGACGATCCGCTCGGACACCTTTGTATCCAGCG
                        TGCGTGAGGTGTTTTACTTCGGTAAATTCAACATCATTGACTGG
                        CAATTCGCCATTCACTATAGCTTTCACCCACGCCACTATGCGAC
                        GGTCATGAACAACCTGTCTGAGCTGACCGCGAGCGGCGGTAAA
                        GTTCTGATCACCACGATGGACGGTGACAAGCTGTCTAAACTGA
                        CCGACAAAAAGACCTTCATTATTCACAAAAATCTCCCGTCGAG
                        CGAGAATTACATGTCCGTCGAAAAGATTGCGGACGACCGTATT
                        GTTGTCTACAACCCGAGCACTATGTCGACCCCAATGACCGAGT
                        ATATCATCAAAAAGAATGACATTGTGCGTGTCTTTAATGAATAC
                        GGTTTTGTGCTGGTCGACAACGTCGATTTTGCGACCATCATCGA
                        GAGAAGCAAGAAATTCATTAATGGCGCTTCTACGATGGAAGAT
                        CGCCCGAGCACGCGTAACTTCTTTGAGCTGAATCGTGGCGCGA
                        TTAAGTGCGAGGGCCTGGACGTCGAGGATCTGCTGTCGTATTA
                        CGTGGTTTATGTGTTTAGCAAACGTTAATGA (SEQ ID NO: 2)
```

Small subunit
(DNA sequence)

```
                        ATGGACGAAATTGTCAAGAATATCCGTGAAGGTACCCACGTTT
                        TACTGCCATTCTACGAGACGCTGCCGGAACTGAACCTGAGCCT
                        GGGTAAAAGCCCTCTGCCGAGCCTGGAGTATGGTGCGAACTAT
                        TTTCTGCAGATTTCCCGTGTAAACGATTTGAACCGCATGCCGAC
                        GGACATGCTGAAACTGTTCACCCACGACATCATGCTGCCGGAA
                        TCTGATCTGGATAAAGTTTACGAGATCTTGAAAATCAATTCAGT
                        GAAGTACTATGGCCGTAGCACCAAGGCCGATGCGGTGGTCGCA
                        GACCTGAGCGCGCGTAACAAACTGTTTAAACGTGAACGTGACG
                        CAATTAAGAGCAATAACCATCTGACCGAGAACAATTTGTACAT
                        CAGCGACTACAAGATGTTGACTTTTGACGTGTTTCGTCCGCTGT
                        TCGACTTTGTTAATGAGAAATACTGCATTATCAAGCTGCCGACG
                        TTGTTTGGTCGCGGCGTCATTGATACGATGCGCATTTACTGCTC
                        TCTCTTCAAGAATGTGCGCCTGCTGAAGTGTGTCTCCGACAGCT
                        GGCTGAAAGATAGCGCTATTATGGTTGCGAGCGACGTGTGTAA
                        AAAGAACCTGGATCTGTTCATGAGCCACGTGAAGAGCGTTACC
                        AAAAGCAGCAGCTGGAAAGACGTTAACAGCGTCCAGTTCTCCA
                        TTCTGAATAACCCGGTCGATACCGAGTTTATCAACAAGTTCCTT
                        GAATTCAGCAATCGCGTTTATGAGGCCCTGTATTACGTTCATAG
                        CCTGCTGTATAGCTCCATGACCTCTGATAGCAAATCGATCGAGA
                        ATAAACACCAACGTCGTCTGGTGAAACTGCTGCTGTAATGA
                        (SEQ ID NO: 3)
```

Thus, in some embodiments, a GT enzyme is a heterodimer comprising large and small subunits (SEQ ID NO: 6 and SEQ ID NO: 7, respectively). In some embodiments, the GT enzyme of the invention may be a homologue or analogue of one or the other of the GT large and small subunits. For example, a homologue or analogue of GT protein may be a modified GT protein containing one or more amino acid substitutions, deletions, and/or insertions as compared to SEQ ID NO: 6 and/or SEQ ID NO: 7, while retaining substantial GT protein activity. Thus, in some embodiments, an enzyme suitable for the present invention is substantially homologous to the GT protein large and small subunits (SEQ ID NO: 6 and SEQ ID NO: 7). In some embodiments, an enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 6. In some embodiments, an enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 7. In some embodiments, an enzyme suitable for the present invention is substantially identical to the large and small subunits of GT (SEQ ID NO: 6 and SEQ ID NO: 7). In some embodiments, an enzyme suitable for the present invention contains a fragment or a portion of a GT protein.

In some embodiments, the GT protein is encoded by a nucleic acid derived from an virus selected from the group consisting of Vaccinia virus, Rabbitpox virus, Cowpox virus, Taterapox virus, Monkeypox virus, Variola major virus, Camelpox virus, Ectromelia virus, Variola minor virus, Orthopox virus, Raccoonpox virus, Skunkpox virus, Volepox virus, Yoka pox virus, Swinepox virus, Yaba monkey tumor virus, Deerpox virus, Myxoma virus, Tanapox virus, Goatpox virus, Rabbit fibroma virus, Lumpy skin disease virus, Sheeppox virus, Eptesipox virus, Squirrelpox virus, Molluscum contagiosum virus, Cotia virus, Orf virus, Bovine popular stomatitis virus, Pseudocowpox virus, Canarypox virus, Pidgeonpox virus, Penguinpox virus, and Fowlpox virus. In some embodiments, nucleic acids suitable for the present invention have a sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 2. In some embodiments, nucleic acids suitable for the present invention have a sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 3. In some embodiments, nucleic acids suitable for the present invention are substantially identical to a nucleic acid encoding a GT protein (SEQ ID NO: 2 and SEQ ID NO: 3).

SUMO-GT Fusion

As used herein, a SUMO-GT fusion protein is any protein or portion of a protein that comprises a SUMO protein covalently linked to a Guanylyl Transferase (GT) protein, wherein the fusion protein can substitute for at least partial activity of naturally-occurring Guanylyl Transferase (GT) protein. As used herein, the terms "a SUMO-GT fusion protein" and "a SUMO-GT fusion enzyme" and grammatical equivalents are used interchangeably. An exemplary amino acid sequence of the fusion of SUMO and the GT large subunit (SEQ ID NO: 8) are shown in Table 3. In addition, an exemplary DNA sequence encoding the fusion of SUMO and the GT large subunit is also provided in Table 3, as SEQ ID NO: 4.

TABLE 3

| SUMO-GT Fusion | |
|---|---|
| SUMO-GT large subunit DNA construct with His tag and linker | ATGGGCCATCATCATCACCATCACGGCAGCCTGCAAGAAGAGA AACCGAAAGAGGGCGTTAAGACCGAGAATGACCACATTAACCT GAAGGTCGCTGGTCAAGATGGCAGCGTGGTGCAGTTTAAGATC AAGCGTCACACGCCGTTGAGCAAGCTGATGAAGGCTTACTGCG AGCGTCAGGGTCTGAGCATGCGTCAGATCCGCTTTCGTTTCGAT GGCCAGCCGATCAATGAGACTGACACCCCAGCGCAACTGGAGA TGGAAGATGAAGATACCATCGACGTCTTTCAGCAACAGACCGG TGGTATGGATGCTAACGTCGTTAGCAGCAGCACCATTGCGACTT ACATTGATGCACTGGCCAAAAACGCATCTGAGCTTGAGCAGCG CAGCACCGCCTACGAGATCAATAACGAATTGGAGCTGGTTTTC ATTAAACCGCCGCTGATCACGCTGACGAACGTCGTGAACATTA GCACGATTCAAGAGAGCTTTATTCGTTTCACCGTTACCAATAAA GAAGGCGTGAAGATCCGTACCAAGATTCCGCTGAGCAAAGTGC ATGGTCTGGACGTGAAAAATGTGCAGCTGGTTGATGCGATCGA TAACATCGTGTGGGAGAAGAAATCTTTGGTCACGGAAAATCGT CTGCACAAGGAATGTCTGCTGCGTCTGTCAACCGAAGAACGCC ACATCTTCCTGGACTACAAGAAGTATGGTTCCAGCATCCGTCTG GAACTGGTGAACCTGATTCAGGCAAAGACCAAGAACTTCACCA TTGACTTCAAACTGAAGTATTTCCTGGGCTCTGGTGCACAGAGC AAATCCAGCTTGTTGCACGCGATTAACCATCCGAAGAGCCGTC CGAATACGAGCCTGGAGATCGAATTCACGCCGCGTGATAACGA AACCGTTCCGTACGATGAGCTGATTAAAGAACTGACGACGTTG AGCCGCCACATCTTTATGGCCAGCCCGGAAAACGTGATCCTTA GCCCGCCTATCAATGCGCCGATTAAAACCTTTATGTTACCGAAA CAAGACATTGTGGGTCTGGACCTGGAAAACCTGTACGCGGTCA CCAAAACGGACGGCATTCCGATCACGATTCGTGTGTTACCAGCAA TGGTCTGTACTGCTATTTCACTCATTTGGGCTATATCATTCGTTA TCCGGTGAAACGCATCATTGATTCTGAGGTTGTCGTTTTCGGCG AAGCAGTCAAGGACAAGAATTGGACTGTGTACCTGATCAAATT GATTGAACCGGTTAACGCCATCAATGACCGCCTGGAAGAGTCG AAATATGTTGAAAGCAAACTGGTGGATATTTGTGATCGTATCGT GTTCAAGAGCAAGAAATATGAAGGCCCGTTCACCACGACCAGC GAAGTTGTTGACATGCTGAGCACCTATCTGCCGAAACAACCTG AGGGTGTGATTCTGTTTTACTCCAAGGGTCCGAAGAGCAACATT GATTTCAAAATCAAGAAAGAGAATACCATTGATCAGACCGCCA ACGTTGTGTTCCGCTATATGTCCAGCGAGCCTATCATTTTCGGT GAGTCGAGCATCTTTGTTGAATACAAAAAGTTTAGCAACGATA AGGGTTTTCCGAAAGAATACGGTTCCGGTAAGATTGTGTTGTAC AACGGCGTCAATTATCTGAACAACATCTACTGTCTGGAGTACAT CAATACCCATAACGAAGTTGGCATTAAGTCTGTTGTCGTCCCGA TCAAATTCATCGCGGAGTTCCTGGTTAACGGTGAGATTCTGAAG CCGCGTATTGATAAAACTATGAAATACATTAACTCCGAAGATT ACTACGGTAATCAGCATAACATCATCGTCGAGCACTTGCGTGA TCAAAGCATTAAGATCGGTGACATCTTTAACGAAGATAAGCTG |

TABLE 3-continued

SUMO-GT Fusion

```
AGCGATGTAGGCCACCAGTATGCGAACAATGACAAATTTCGCC
TGAATCCGGAAGTCAGCTACTTTACGAATAAGCGCACCCGTGG
TCCACTGGGTATCCTGAGCAATTATGTTAAAACCCTGTTGATTT
CCATGTACTGCTCCAAAACGTTCCTGGACGACAGCAACAAGCG
CAAAGTTCTGGCGATCGACTTCGGTAATGGTGCCGATCTGGAG
AAGTACTTTTATGGTGAGATCGCATTGCTGGTTGCTACCGACCC
GGATGCAGATGCGATCGCCCGTGGCAACGAGCGTTACAATAAG
CTGAATAGCGGTATCAAGACCAAATACTACAAATTCGACTATA
TTCAAGAGACGATCCGCTCGGACACCTTTGTATCCAGCGTGCGT
GAGGTGTTTTACTTCGGTAAATTCAACATCATTGACTGGCAATT
CGCCATTCACTATAGCTTTCACCCACGCCACTATGCGACGGTCA
TGAACAACCTGTCTGAGCTGACCGCGAGCGGCGGTAAAGTTCT
GATCACCACGATGGACGGTGACAAGCTGTCTAAACTGACCGAC
AAAAAGACCTTCATTATTCACAAAAATCTCCCGTCGAGCGAGA
ATTACATGTCCGTCGAAAAGATTGCGGACGACCGTATTGTTGTC
TACAACCCGAGCACTATGTCGACCCCAATGACCGAGTATATCA
TCAAAAAGAATGACATTGTGCGTGTCTTTAATGAATACGGTTTT
GTGCTGGTCGACAACGTCGATTTTGCGACCATCATCGAGAGAA
GCAAGAAATTCATTAATGGCGCTTCTACGATGGAAGATCGCCC
GAGCACGCGTAACTTCTTTGAGCTGAATCGTGGCGCGATTAAG
TGCGAGGGCCTGGACGTCGAGGATCTGCTGTCGTATTACGTGG
TTTATGTGTTTAGCAAACGTTAATGA (SEQ ID NO: 4)
```

SUMO-GT large
subunit protein
with His tag and
linker

```
MGHHHHHHGSLQEEKPKEGVKTENDHINLKVAGQDGSVVQFKIK
RHTPLSKLMKAYCERQGLSMRQIRFRFDGQPINETDTPAQLEMED
EDTIDVFQQQTGGMDANVVSSSTIATYIDALAKNASELEQRSTAY
EINNELELVFIKPPLITLTNVVNISTIQESFIRFTVTNKEGVKIRTKIPL
SKVHGLDVKNVQLVDAIDNIVWEKKSLVTENRLHKECLLRLSTEE
RHIFLDYKKYGSSIRLELVNLIQAKTKNFTIDFKLKYFLGSGAQSKS
SLLHAINHPKSRPNTSLEIEFTPRDNETVPYDELIKELTTLSRHIFMA
SPENVILSPPINAPIKTFMLPKQDIVGLDLENLYAVTKTDGIPITIRV
TSNGLYCYFTHLGYIIRYPVKRIIDSEVVVFGEAVKDKNWTVYLIK
LIEPVNAINDRLEESKYVESKLVDICDRIVFKSKKYEGPFTTTSEVV
DMLSTYLPKQPEGVILFYSKGPKSNIDFKIKKENTIDQTANVVFRY
MSSEPIIFGESSIPVEYKKFSNDKGFPKEYGSGKIVLYNGVNYLNNI
YCLEYINTHNEVGIKSVVVPIKFIAEFLVNGEILKPRIDKTMKYINSE
DYYGNQHNIIVEHLRDQSIKIGDIFNEDKLSDVGHQYANNDKFRL
NPEVSYFTNKRTRGPLGILSNYVKTLLISMYCSKTFLDDSNKRKVL
AIDFGNGADLEKYFYGEIALLVATDPDADAIARGNERYNKLNSGI
KTKYYKFDYIQETIRSDTFVSSVREVFYFGKFNIIDWQFAIHYSFHP
RHYATVMNNLSELTASGGKVLITTMDGDKLSKLTDKKTFIIHKNL
PSSENYMSVEKIADDRIVVYNPSTMSTPMTEYIIKKNDIVRVFNEY
GFVLVDNVDFATIIERSKKFINGASTMEDRPSTRNFFELNRGAIKCE
GLDVEDLLSYYVVYVFSKR (SEQ ID NO: 8)
```

In some embodiments, the SUMO-GT fusion protein comprises SEQ ID NO: 8. In some embodiments, the SUMO-GT fusion protein is a heterodimer comprising SEQ ID NO: 8 and SEQ ID NO: 7. In some embodiments, the GT enzyme of the invention may be a homologue or analogue of one or the other of the GT large and small subunits. For example, a homologue or analogue of the SUMO-GT fusion protein may be a modified SUMO-GT fusion protein containing one or more amino acid substitutions, deletions, and/or insertions as compared to SEQ ID NO: 8 and/or SEQ ID NO: 7, while retaining substantial GT protein activity. Thus, in some embodiments, a SUMO-GT fusion protein suitable for the present invention is substantially homologous to the heterodimer comprising the GT small subunit (SEQ ID NO: 7) and the fusion of SUMO and the GT large subunit (SEQ ID NO: 8). In some embodiments, an enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO: 8 and SEQ ID NO: 7. In some embodiments, an enzyme suitable for the present invention is substantially identical to the heterodimer comprising the GT small subunit (SEQ ID NO: 7) and the fusion of SUMO and the GT large subunit (SEQ ID NO: 8). In some embodiments, an enzyme suitable for the present invention contains a fragment or a portion of a GT protein covalently bound to a SUMO protein.

Production of SUMO-GT Fusion Protein

Host Cells

As used herein, the term "host cells" refers to cells that can be used to produce a SUMO-GT fusion protein. In particular, host cells are suitable for producing a SUMO-GT fusion protein at a large scale. In some embodiments, host cells are able to produce SUMO-GT fusion protein in an amount of or greater than about 5 picogram/cell/day (e.g., greater than about 10, 15, 20, 25, 30, 35, 40, 45, 50, 55, 60, 65, 70, 75, 80, 85, 90, 95, or 100 picogram/cell/day). In some embodiments, host cells are able to produce SUMO-GT fusion protein in an amount ranging from about 5-100 picogram/cell/day (e.g., about 5-90 picogram/cell/day, about 5-80 picogram/cell/day, about 5-70 picogram/cell/day, about 5-60 picogram/cell/day, about 5-50 picogram/cell/day, about 5-40 picogram/cell/day, about 5-30 picogram/cell/day, about 10-90 picogram/cell/day, about 10-80 picogram/cell/day, about 10-70 picogram/cell/day, about 10-60 picogram/cell/day, about 10-50 picogram/cell/day, about 10-40 picogram/cell/day, about 10-30 picogram/cell/day, about 20-90 picogram/cell/day, about 20-80 picogram/cell/day, about 20-70 picogram/cell/day, about 20-60 picogram/cell/day, about 20-50 picogram/cell/day, about 20-40 picogram/cell/day, about 20-30 picogram/cell/day).

Suitable host cells can be derived from a variety of organisms, including, but not limited to, bacteria, yeast, insects, plants, birds (e.g., avian systems), amphibians, and mammals. In some embodiments, host cells are non-mammalian cells. Non-limiting examples of non-mammalian host cells suitable for the present invention include cells and cell lines derived from *Escherichia coli, Salmonella typhimurium, Bacillus subtilis, Bacillus licheniformis, Bacteroides fragilis, Clostridia perfringens, Clostridia difficile* for bacteria; *Pichia pastoris, Pichia methanolica, Pichia angusta, Schizosaccharomyces pombe, Saccharomyces cerevisiae,* and *Yarrowia lipolytica* for yeast; *Sodoptera frugiperda, Trichoplusis ni, Drosophila melangoster* and *Manduca sexta* for insects; and and *Xenopus Laevis* from amphibian.

In some embodiments, host cells are mammalian cells. Any mammalian cell susceptible to cell culture, and to expression of polypeptides, may be utilized in accordance with the present invention as a host cell. Non-limiting examples of mammalian cells that may be used in accordance with the present invention include human embryonic kidney 293 cells (HEK293), HeLa cells; BALB/c mouse myeloma line (NSO/l, ECACC No: 85110503); human retinoblasts (PER.C6 (CruCell, Leiden, The Netherlands)); monkey kidney CVI line transformed by SV40 (COS-7, ATCC CRL 1651); human fibrosarcomacell line (e.g., HT-1080); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells +/−DHFR (CHO, Urlaub and Chasin, Proc. Natl. Acad. Sci. USA, 77:4216 (1980)); mouse sertoli cells (TM4, Mather, Biol. Reprod., 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); MRC 5 cells; FS4 cells; a human hepatoma line (Hep G2), human cell line CAP and AGE1. HN, and Glycotope's panel.

Additionally, any number of available hybridoma cell lines may be utilized in accordance with the present invention. One skilled in the art will appreciate that hybridoma cell lines might have different nutrition requirements and/or might require different culture conditions for optimal growth and polypeptide or protein expression, and will be able to modify conditions as needed.

Expression Vectors

Various nucleic acid constructs can be used to express SUMO-GT fusion protein described herein in host cells. A suitable vector construct typically includes, in addition to SUMO-GT fusion protein-encoding sequences (also referred to as SUMO-GT fusion transgene), regulatory sequences, gene control sequences, promoters, non-coding sequences and/or other appropriate sequences for expression of the protein and, optionally, for replication of the construct. Typically, the coding region is operably linked with one or more of these nucleic acid components.

"Regulatory sequences" typically refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, 5' untranslated sequences, translation leader sequences, introns, and 3' untranslated sequences such as polyadenylation recognition sequences. Sometimes, "regulatory sequences" are also referred to as "gene control sequences."

"Promoter" typically refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions.

The "3' non-coding sequences" typically refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The "translation leader sequence" or "5' non-coding sequences" typically refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

Typically, the term "operatively linked" refers to the association of two or more nucleic acid fragments on a single nucleic acid fragment so that the function of one is affected by the other. For example, a promoter is operatively linked with a coding sequence when it is capable of affecting the expression of that coding sequence (i.e., that the coding sequence is under the transcriptional control of the promoter). Coding sequences can be operatively linked to regulatory sequences in sense or antisense orientation.

The coding region of a transgene may include one or more silent mutations to optimize codon usage for a particular cell type. For example, the codons of an SUMO-GT fusion transgene may be optimized for expression in a bacterial cell. In some embodiments, the codons of an SUMO-GT fusion transgene may be optimized for expression in an *E. coli* cell. In some embodiments, the codons of an SUMO-GT fusion transgene may be optimized for expression in a mammalian cell. In some embodiments, the codons of an SUMO-GT fusion transgene may be optimized for expression in a human cell.

Optionally, a construct may contain additional components such as one or more of the following: a splice site, an enhancer sequence, a selectable marker gene under the control of an appropriate promoter, an amplifiable marker gene under the control of an appropriate promoter, and a matrix attachment region (MAR) or other element known in the art that enhances expression of the region where it is inserted.

Once transfected or transduced into host cells, a suitable vector can express extrachromosomally (episomally) or integrate into the host cell's genome.

In some embodiments, a DNA construct that integrates into the cell's genome, it need include only the transgene nucleic acid sequences. In that case, the express of the transgene is typically controlled by the regulatory sequences at the integration site. Optionally, it can include additional various regulatory sequences described herein.

Culture Medium and Conditions

The term "medium" and "culture medium" as used herein refers to a general class of solution containing nutrients suitable for maintaining and/or growing cells in vitro. Typically, medium solutions provide, without limitation, essential and nonessential amino acids, vitamins, energy sources, lipids, and trace elements required by the cell for at least minimal growth and/or survival. In other embodiments, the medium may contain an amino acid(s) derived from any source or method known in the art, including, but not limited to, an amino acid(s) derived either from single amino acid addition(s) or from a peptone or protein hydrolysate addition (s) (including animal or plant source(s)). Vitamins such as, but not limited to, Biotin, Pantothenate, Choline Chloride, Folic Acid, Myo-Inositol, Niacinamide, Pyridoxine, Ribo-flavin, Vitamin B12, Thiamine, Putrescine and/or combinations thereof. Salts such as, but not limited to, $CaCl_2$, KCl, $MgCl_2$, NaCl, Sodium Phosphate Monobasic, Sodium Phosphate Dibasic, Sodium Selenite, $CuSO_4$, $ZnCl_2$ and/or combinations thereof. Fatty acids such as, but not limited to, Arachidonic Acid, Linoleic Acid, Oleic Acid, Lauric Acid, Myristic Acid, as well as Methyl-beta-Cyclodextrin and/or combinations thereof). In some embodiments, medium comprises additional components such as glucose, glutamine, Na-pyruvate, insulin or ethanolamine, a protective agent such as Pluronic F68. In some embodiments, the medium may also contain components that enhance growth and/or survival above the minimal rate, including hormones and growth factors. Medium may also comprise one or more buffering agents. The buffering agents may be designed and/or selected to maintain the culture at a particular pH (e.g., a physiological pH, (e.g., pH 6.8 to pH 7.4)). A variety of buffers suitable for culturing cells are known in the art and may be used in the methods. Suitable buffers (e.g., bicarbonate buffers, HEPES buffer, Good's buffers, etc.) are those that have the capacity and efficiency for maintaining physiological pH despite changes in carbon dioxide concentration associated with cellular respiration. The solution is preferably formulated to a pH and salt concentration optimal for cell survival and proliferation.

In some embodiments, medium may be a chemically defined medium. As used herein, the term "chemically-defined nutrient medium" refers to a medium of which substantially all of the chemical components are known. In some embodiments, a chemically defined nutrient medium is free of animal-derived components. In some cases, a chemically-defined medium comprises one or more proteins (e.g., protein growth factors or cytokines.) In some cases, a chemically-defined nutrient medium comprises one or more protein hydrolysates. In other cases, a chemically-defined nutrient medium is a protein-free media, i.e., a serum-free media that contains no proteins, hydrolysates or components of unknown composition.

Typically, a chemically defined medium can be prepared by combining various individual components such as, for example, essential and nonessential amino acids, vitamins, energy sources, lipids, salts, buffering agents, and trace elements, at predetermined weight or molar percentages or ratios. Exemplary serum-free, in particular, chemically-defined media are described in US Pub. No. 2006/0148074, the disclosure of which is hereby incorporated by reference.

In some embodiments, a chemically defined medium suitable for the present invention is a commercially available medium such as, but not limited to, Terrific Broth, Cinnabar, 2×YT or LB. In some embodiments, a chemically defined medium suitable for the present invention is a mixture of one or more commercially available chemically defined mediums. In various embodiments, a suitable medium is a mixture of two, three, four, five, six, seven, eight, nine, ten, or more commercially available chemically defined media. In some embodiments, each individual commercially available chemically defined medium (e.g., such as those described herein) constitutes, by weight, 1%, 2.5%, 5%, 7.5%, 10%, 12.5%, 15%, 20%, 25%, 30%, 35%, 40%, 45%, 50%, 55%, 60%, 65%, 70%, 75%, 80%, 85%, 90%, 95%, or more, of the mixture. Ratios between each individual component medium may be determined by relative weight percentage present in the mixture. In some embodiments, protein expression is increased with the addition of IPTG to repress the promoter.

In some embodiments, a chemically defined medium may be supplemented by one or more animal derived components. Such animal derived components include, but are not limited to, fetal calf serum, horse serum, goat serum, donkey serum, human serum, and serum derived proteins such as albumins (e.g., bovine serum albumin or human serum albumin).

The present invention provides a method of producing SUMO-GT fusion protein at a large scale. Typical large-scale procedures for producing a fusion polypeptide of interest include batch cultures and fed-batch cultures. Batch culture processes traditionally comprise inoculating a large-scale production culture with a seed culture of a particular cell density, growing the cells under conditions (e.g., suitable culture medium, pH, and temperature) conducive to cell growth, viability, and/or productivity, harvesting the culture when the cells reach a specified cell density, and purifying the expressed polypeptide. Fed-batch culture procedures include an additional step or steps of supplementing the batch culture with nutrients and other components that are consumed during the growth of the cells. In some embodiments, a large-scale production method according to the present invention uses a fed-batch culture system.

Purification of Expressed SUMO-GT Fusion Protein

Various methods may be used to purify or isolate SUMO-GT fusion protein produced according to various methods described herein. In some embodiments, the expressed SUMO-GT fusion protein is secreted into the medium and thus cells and other solids may be removed, as by centrifugation or filtering for example, as a first step in the purification process. Alternatively or additionally, the expressed SUMO-GT fusion protein is bound to the surface of the host cell. In this embodiment, the host cells (for example, bacterials cells) expressing the polypeptide or protein are lysed for purification. Lysis of host cells (e.g., bacterials cells) can be achieved by any number of means well known to those of ordinary skill in the art, including physical disruption by glass beads and exposure to high pH conditions.

The SUMO-GT fusion protein may be isolated and purified by standard methods including, but not limited to, chromatography (e.g., ion exchange, affinity, size exclusion, and hydroxyapatite chromatography), gel filtration, centrifugation, or differential solubility, ethanol precipitation or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference). For immunoaffinity chromatography in particular, the protein may be isolated by binding it to an affinity column comprising antibodies that were raised against that protein and were affixed to a stationary support. Protease inhibitors such as phenyl methyl sulfonyl fluoride (PMSF), leupeptin, pepstatin or aprotinin may be added at any or all stages in order to reduce or eliminate degradation of the polypeptide or protein during the purification process. Protease inhibitors are particularly desired when cells must be lysed in order to isolate and purify the expressed polypeptide or protein.

Solubility

Various methods may be used to determine the solubility of a protein in an expression system. In an exemplary method, bacteria are spun down and resuspended in a mild lysis buffer containing 1% IGEPAL and protease inhibitors. Lysis is supported by repeated freezing and thawing the bacteria. Soluble and insoluble fraction are separated by centrifigation. To determine the total amount of recombinant protein the same volume of bacterial culture is spun down and lysed in the same amount of lysis buffer containing 1% IGEPAL and 0.1% SDS. Soluble and total protein are analyzed by SDS-PAGE, with western blotting if necessary. In some embodiments, the expression system is *E. coli*. In some embodiments, solubility of GT is improved when it has been produced as a fusion protein. In some embodiments, the fusion protein is a SUMO-GT fusion protein. In some embodiments, the SUMO-GT fusion protein has increased solubility compared to the non-fusion GT protein. In some embodiments, the increased solubility of the SUMO-GT fusion protein compared to the non-fusion GT protein is observed during shake flask production of the SUMO-GT fusion protein. In some embodiments, the increased solubility of the SUMO-GT fusion protein compared to the non-fusion GT protein is observed during fermentation production of the SUMO-GT fusion protein.

Use of SUMO-GT Fusion in mRNA Capping

Production of Capped mRNAs

According to the present invention, a SUMO-GT fusion protein described herein may be used to produce capped mRNAs by in vitro transcription. Various in vitro transcription assays are available in the art and can be used to practice the present invention. For example, in vitro transcription was originally developed by Krieg and Melton (METHODS ENZYMOL., 1987, 155:397-415) for the synthesis of RNA using an RNA phage polymerase. Typically these reactions include at least a phage RNA polymerase (T7, T3 or SP6), a DNA template containing a phage polymerase promoter, nucleotides (ATP, CTP, GTP and UTP), and a buffer containing a magnesium salt. RNA synthesis yields may be optimized by increasing nucleotide concentrations, adjusting magnesium concentrations and by including inorganic pyrophosphatase (U.S. Pat. No. 5,256,555; Gurevich, et al., ANAL. BIOCHEM. 195:207-213 (1991); Sampson, J. R. and Uhlenbeck, O. C., PROC. NATL. ACAD. SCI. USA. 85, 1033-1037 (1988); Wyatt, J. R., et al., BIOTECHNIQUES, 11:764-769 (1991)). The RNA synthesized in these reactions is usually characterized by a 5' terminal nucleotide that has a triphosphate at the 5' position of the ribose. Typically, depending on the RNA polymerase and promoter combination used, this nucleotide is a guanosine, although it can be an adenosine (see e.g., Coleman, T. M., et al., NUCLEIC ACIDS RES., 32: e14 (2004)). In these reactions, all four nucleotides are typically included at equimolar concentrations and none of them is limiting.

Some embodiment of the invention are batch reactions-that is, all components are combined and then incubated at about 37° C. to promote the polymerization of the RNA until the reaction terminates. Typically, a batch reaction is used for convenience and to obtain as much RNA as needed from such reactions for their experiments. In some embodiments, a "fed-batch" system (see, e.g., JEFFREY A. KERN, BATCH AND FED-BATCH STRATEGIES FOR LARGE-SCALE PRODUCTION OF RNA BY IN VITRO TRANS-ACTION (University of Colorado) (1997)) is used to increase the efficiency of the in vitro transcription reaction. All components are combined, but then additional amounts of some of the reagents are added over time, such as the nucleotides and magnesium, to try to maintain constant reaction conditions. In addition, in some embodiments, the pH of the reaction may be held at 7.4 by monitoring it over time and adding KOH as needed.

To synthesize a capped RNA by in vitro transcription, a cap analog (e.g., N-7 methyl GpppG; i.c., $m^7$GpppG) is included in the transcription reaction. In some embodiments, the cap analog will be incorporated at the 5' terminus by the enzyme guanylyl transferase. In some embodiments, the guanylyl transferase is a fusion protein. In some embodiments, the guanylyl transferase fusion protein formed when a guanylyl transferase is covalently linked to a SUMO protein. In some embodiments, the cap analog will be incorporated only at the 5' terminus because it does not have a 5' triphosphate. In some embodiments using a T7, T3 and SP6 RNA polymerase, the +1 nucleotide of their respective promoters is usually a G residue and if both GTP and m7GpppG are present in equal concentrations in the transcription reaction, then they each have an equal chance of being incorporated at the +1 position. In some embodiments, $m^7$GpppG is present in these reactions at several-fold higher concentrations than the GTP to increase the chances that a transcript will have a 5' cap. In some embodiments, a mMESSAGE mMACHINE® kit (Cat. #1344, Ambion, Inc.) is used according to manufacturer's instructions, where it is recommended that the cap to GTP ratio be 4:1 (6 mM:1.5 mM). In some embodiments, as the ratio of the cap analog to GTP increases in the reaction, the ratio of capped to uncapped RNA increases proportionally. Considerations of capping efficiency must be balanced with considerations of yield. Increasing the ratio of cap analog to GTP in the transcription reaction produces lower yields of total RNA because the concentration of GTP becomes limiting when holding the total concentration of cap and GTP constant. Thus, the final RNA yield is dependent on GTP concentration, which is necessary for the elongation of the transcript. The other nucleotides (ATP, CTP, UTP) are present in excess.

Figures 1A, 1B:
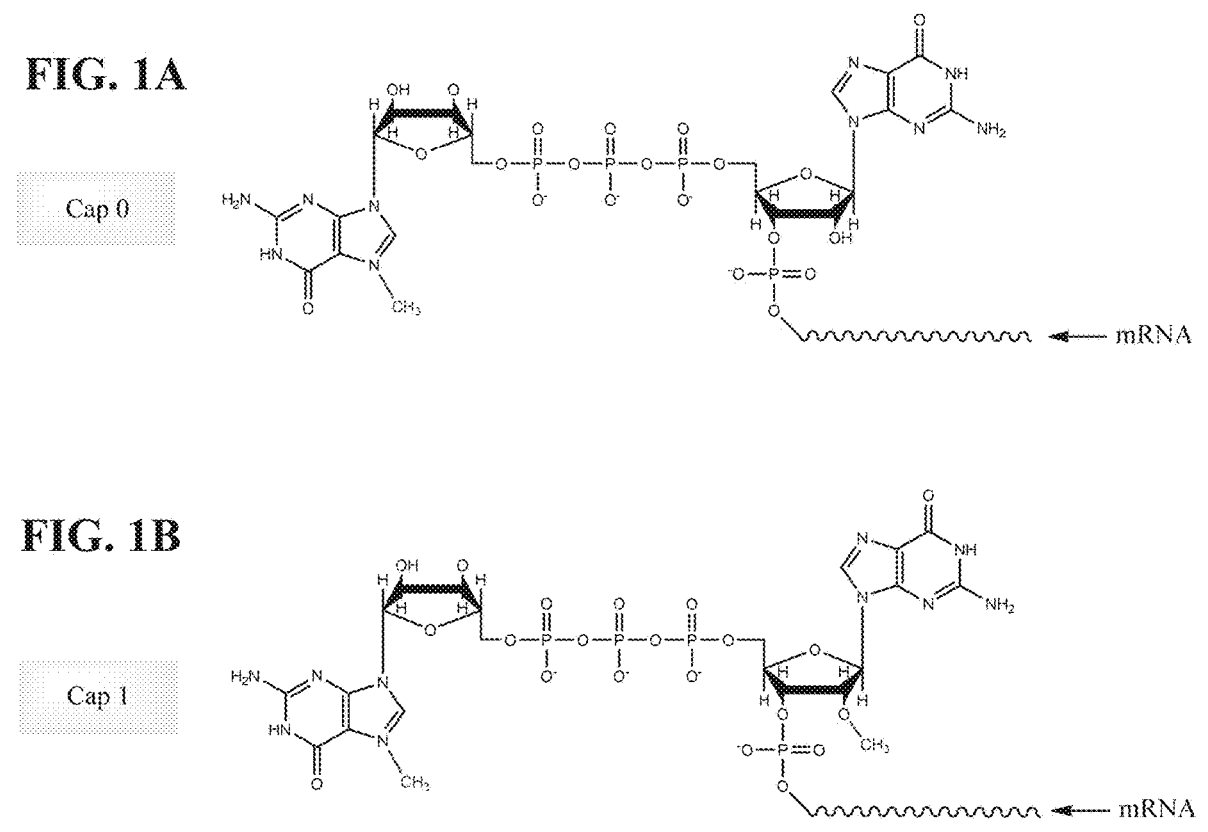

In particular embodiments, mRNA are synthesized by in vitro transcription from a plasmid DNA template encoding a gene of choice. In some embodiments, in vitro transcription includes addition of a 5' cap structure, Cap1 (FIG. 1B), which has a 2'-O-methyl residue at the 2' OH group of the ribose ring of base 1, by enzymatic conjugation of GTP via a guanylyl transferase. In some embodiments, in vitro transcription includes addition of a 5' cap structure, Cap0 (FIG. 1A), which lacks the 2'-O-methyl residue, by enzymatic conjugation of GTP via a guanylyl transferase. In some embodiments, in vitro transcription includes addition of a 5' cap of any of the cap structures disclosed herein by enzymatic conjugation of GTP via a guanylyl transferase.

Capping Efficiency

The present invention significantly increases capping efficiency. In some embodiments, the use of a SUMO-GT fusion protein in an in vitro capping assay results in at least about 70%, 75%, 80%, 85%, 90%, 95%, 96%, 97%, 98%, or 99% capped mRNA. In some embodiments, the use of a SUMO-GT fusion protein in an in vitro capping assay results in substantially 100% capped mRNA. In some embodiments, the use of a SUMO-GT fusion protein in an in vitro capping assay results in increase of mRNA capping efficiency by at least about 20%, 30%, 40%, 50%, 60%, 70%, 80%, 90%, 95%, 1-fold, 1.5-fold, 2-fold, 2.5-fold, 3-fold, 3.5-fold, 4-fold, 4.5-fold, or 5-fold as compared to a control assay using a non-fusion GT protein but under otherwise identical conditions.

In addition, the present invention permits large-scale production of capped mRNA with high efficiency. In some embodiments, capped mRNA is produced at a scale of or greater than 1 gram, 5 grams, 10 grams, 15 grams, 20 grams, 25 grams, 30 grams, 35 grams, 40 grams, 45 grams, 50 grams, 75 grams, 100 grams, 150 grams, 200 grams, 250 grams, 300 grams, 350 grams, 400 grams, 450 grams, 500 grams, 550 grams, 600 grams, 650 grams, 700 grams, 750 grams, 800 grams, 850 grams, 900 grams, 950 grams, 1 kg, 2.5 kg, 5 kg, 7.5 kg, 10 kg, 25 kg, 50 kg, 75 kg, or 100 kg per batch.

Methods of estimating capping efficiency are known in the art. For example, the T7 RNA polymerase can be incubated with a cap dinucleotide, all four ribonucleotide triphosphates, [$\alpha$-$^{32}$P]GTP, and a short DNA template in which G is the first ribonucleotide specified after the promoter (see Grudzien, E. et al. "*Novel cap analogs for in vitro synthesis of mRNA with high translation efficiency*", RNA, 10:1479-1487 (2004)). Any nucleotide on the 5' side of a G residue acquires a $^{32}$P-labeled 3'-phosphate group after RNase T2 digestion by nearest-neighbor transfer. Anion exchange chromatography is then used to resolve labeled nucleoside 3'-monophosphates, resulting from internal positions in the RNA, from 5'-terminal products. 5'-terminal products are of two types. Uncapped RNAs yield labeled guanosine 5'-triphosphate 3'-monophosphate (p3Gp*; in which * indicates the labeled phosphate group). Capped RNAs yield various 5'-terminal structures, depending on the nature of the cap analog used (m$^7$Gp3Gp* and Gp3m$^7$Gp* when the cap analog is m$^7$Gp3G).

Improved methods of directly quantitating mRNA capping efficiency in a sample (e.g., a representative aliquot sample from an in vitro synthesis reaction) are provided in WO 2014/152673, which is incorporated herein by reference. Some embodiments comprise the use of a cap specific binding substance under conditions that permit the formation of a complex between the cap specific binding substance and the capped mRNA. The formation of a complex between the cap specific binding substance and the capped mRNA allows quantitative determination of the amount of the complex (i.e., capped mRNAs) relative to a positive control of capped products or negative control of uncapped products. In other words, binding indicates the amount of capped mRNA targets in the sample and the capping efficiency in a reaction from which the sample is derived. Thus, in some embodiments, the step of quantitatively determining the amount of the complex comprises performing an ELISA-type assay wherein the cap specific binding substance is an antibody or other protein that specifically binds an mRNA cap. Complex formation can be quantified by addition of a detection agent specific for the cap specific binding substance (e.g., a goat anti-mouse antibody that binds a mouse anti-m$^7$G antibody) and which produces a signal directly proportional to the amount of capped mRNA. Embodiments of the invention may be used to quantify the capping efficiency of a wide variety of RNA species, including in vitro transcribed mRNA, isolated eukaryotic mRNA, and viral RNA.

Additional improved methods of directly quantitating mRNA capping efficiency in a sample (e.g., a representative aliquot sample from an in vitro synthesis reaction) are provided in WO 2014/152659, which is incorporated herein by reference. Some embodiments of the invention comprise chromatographic methods of quantitating mRNA capping efficiency. These methods are based in part on the insights that the versatility of enzymatic manipulation can be used to increase the resolution of chromatographic separation of polynucleotides. Thus, by amplifying the power of chromatographic separation through enzymatic manipulation, embodiments of the invention increase the efficiency, quality and throughput of quantitation. For example, not only can the chromatographic methods described herein quantitate capping efficiency, they can also provide information on the modification of the cap (e.g., methylation status at particular cap positions). Thus, embodiments of the invention can simultaneously quantitate capping efficiency and the efficiency of cap modification (e.g., methylation efficiency). This quantification provides important characterization of an mRNA drug product that has significant impact on the protein production.

The invention will be more fully understood by reference to the following examples. They should not, however, be construed as limiting the scope of the invention. All literature citations are incorporated by reference.

EXAMPLES

Example 1: SUMO-GT Construct Design

A new construct incorporating a small ubiquitin-like modifier (SUMO) tag covalently linked and co-expressed with the large subunit faction of a guanylyl transferase (GT) heterodimer was synthesized.

```
Small ubiquitin-like modifier (SUMO) DNA:
                                      (SEQ ID NO: 5)
GAAGAGAAACCGAAAGAGGGCGTTAAGACCGAGAATGACCACATTAACCTGAAGG

TCGCTGGTCAAGATGGCAGCGTGGTGCAGTTTAAGATCAAGCGTCACACGCCGTTGA

GCAAGCTGATGAAGGCTTACTGCGAGCGTCAGGGTCTGAGCATGCGTCAGATCCGC

TTTCGTTTCGATGGCCAGCCGATCAATGAGACTGACACCCCAGCGCAACTGG

Guanylyl transferase (GT) large subunit DNA:
```

-continued (SEQ ID NO: 2)

```
AGATGGAAGATGAAGATACCATCGACGTCTTTCAGCAACAGACCGGTGGTATGGAT

GCTAACGTCGTTAGCAGCAGCACCATTGCGACTTACATTGATGCACTGGCCAAAAAC

GCATCTGAGCTTGAGCAGCGCAGCACCGCCTACGAGATCAATAACGAATTGGAGCT

GGTTTTCATTAAACCGCCGCTGATCACGCTGACGAACGTCGTGAACATTAGCACGAT

TCAAGAGAGCTTTATTCGTTTCACCGTTACCAATAAAGAAGGCGTGAAGATCCGTAC

CAAGATTCCGCTGAGCAAAGTGCATGGTCTGGACGTGAAAAATGTGCAGCTGGTTG

ATGCGATCGATAACATCGTGTGGGAGAAGAAATCTTTGGTCACGGAAAATCGTCTG

CACAAGGAATGTCTGCTGCGTCTGTCAACCGAAGAACGCCACATCTTCCTGGACTAC

AAGAAGTATGGTTCCAGCATCCGTCTGGAACTGGTGAACCTGATTCAGGCAAAGAC

CAAGAACTTCACCATTGACTTCAAACTGAAGTATTTCCTGGGCTCTGGTGCACAGAG

CAAATCCAGCTTGTTGCACGCGATTAACCATCCGAAGAGCCGTCCGAATACGAGCCT

GGAGATCGAATTCACGCCGCGTGATAACGAAACCGTTCCGTACGATGAGCTGATTA

AAGAACTGACGACGTTGAGCCGCCACATCTTTATGGCCAGCCCGGAAAACGTGATC

CTTAGCCCGCCTATCAATGCGCCGATTAAAAACCTTTATGTTACCGAAACAAGACATT

GTGGGTCTGGACCTGGAAAACCTGTACGCGGTCACCAAAACGGACGGCATTCCGAT

CACGATTCGTGTTACCAGCAATGGTCTGTACTGCTATTTCACTCATTTGGGCTATATC

ATTCGTTATCCGGTGAAACGCATCATTGATTCTGAGGTTGTCGTTTTCGGCGAAGCA

GTCAAGGACAAGAATTGGACTGTGTACCTGATCAAATTGATTGAACCGGTTAACGCC

ATCAATGACCGCCTGGAAGAGTCGAAATATGTTGAAAGCAAACTGGTGGATATTTG

TGATCGTATCGTGTTCAAGAGCAAGAAATATGAAGGCCCGTTCACCACGACCAGCG

AAGTTGTTGACATGCTGAGCACCTATCTGCCGAAACAACCTGAGGGTGTGATTCTGT

TTTACTCCAAGGGTCCGAAGAGCAACATTGATTTCAAAATCAAGAAAGAGAATACC

ATTGATCAGACCGCCAACGTTGTGTTCCGCTATATGTCCAGCGAGCCTATCATTTTCG

GTGAGTCGAGCATCTTTGTTGAATACAAAAAGTTTAGCAACGATAAGGGTTTTCCGA

AAGAATACGGTTCCGGTAAGATTGTGTTGTACAACGGCGTCAATTATCTGAACAACA

TCTACTGTCTGGAGTACATCAATACCCATAACGAAGTTGGCATTAAGTCTGTTGTCG

TCCCGATCAAATTCATCGCGGAGTTCCTGGTTAACGGTGAGATTCTGAAGCCGCGTA

TTGATAAAACTATGAAATACATTAACTCCGAAGATTACTACGGTAATCAGCATAACA

TCATCGTCGAGCACTTGCGTGATCAAAGCATTAAGATCGGTGACATCTTTAACGAAG

ATAAGCTGAGCGATGTAGGCCACCAGTATGCGAACAATGACAAATTTCGCCTGAAT

CCGGAAGTCAGCTACTTTACGAATAAGCGCACCCGTGGTCCACTGGGTATCCTGAGC

AATTATGTTAAAACCCTGTTGATTTCCATGTACTGCTCCAAAAACGTTCCTGGACGAC

AGCAACAAGCGCAAAGTTCTGGCGATCGACTTCGGTAATGGTGCCGATCTGGAGAA

GTACTTTTATGGTGAGATCGCATTGCTGGTTGCTACCGACCCGGATGCAGATGCGAT

CGCCCGTGGCAACGAGCGTTACAATAAGCTGAATAGCGGTATCAAGACCAAATACT

ACAAATTCGACTATATTCAAGAGACGATCCGCTCGGACACCTTTGTATCCAGCGTGC

GTGAGGTGTTTTTACTTCGGTAAATTCAACATCATTGACTGGCAATTCGCCATTCACTA

TAGCTTTCACCCACGCCACTATGCGACGGTCATGAACAACCTGTCTGAGCTGACCGC

GAGCGGCGGTAAAGTTCTGATCACCACGATGGACGGTGACAAGCTGTCTAAACTGA

CCGACAAAAAGACCTTCATTATTCACAAAAATCTCCCGTCGAGCGAGAATTACATGT
```

-continued

CCGTCGAAAAGATTGCGGACGACCGTATTGTTGTCTACAACCCGAGCACTATGTCGA

CCCCAATGACCGAGTATATCATCAAAAAGAATGACATTGTGCGTGTCTTTAATGAAT

ACGGTTTTGTGCTGGTCGACAACGTCGATTTTGCGACCATCATCGAGAGAAGCAAGA

AATTCATTAATGGCGCTTCTACGATGGAAGATCGCCCGAGCACGCGTAACTTCTTTG

AGCTGAATCGTGGCGCGATTAAGTGCGAGGGCCTGGACGTCGAGGATCTGCTGTCG

TATTACGTGGTTTATGTGTTTAGCAAACGTTAATGA

Guanylyl transferase (GT) small subunit DNA:

(SEQ ID NO: 3)

ATGGACGAAATTGTCAAGAATATCCGTGAAGGTACCCACGTTTTACTGCCATTCTAC

GAGACGCTGCCGGAACTGAACCTGAGCCTGGGTAAAAGCCCTCTGCCGAGCCTGGA

GTATGGTGCGAACTATTTTCTGCAGATTTCCCGTGTAAACGATTTGAACCGCATGCC

GACGGACATGCTGAAACTGTTCACCCACGACATCATGCTGCCGGAATCTGATCTGGA

TAAAGTTTACGAGATCTTGAAAATCAATTCAGTGAAGTACTATGGCCGTAGCACCAA

GGCCGATGCGGTGGTCGCAGACCTGAGCGCGCGTAACAAACTGTTTAAACGTGAAC

GTGACGCAATTAAGAGCAATAACCATCTGACCGAGAACAATTTGTACATCAGCGAC

TACAAGATGTTGACTTTTGACGTGTTTCGTCCGCTGTTCGACTTTGTTAATGAGAAAT

ACTGCATTATCAAGCTGCCGACGTTGTTTGGTCGCGGCGTCATTGATACGATGCGCA

TTTACTGCTCTCTCTTCAAGAATGTGCGCCTGCTGAAGTGTGTCTCCGACAGCTGGCT

GAAAGATAGCGCTATTATGGTTGCGAGCGACGTGTGTAAAAAGAACCTGGATCTGT

TCATGAGCCACGTGAAGAGCGTTACCAAAAGCAGCAGCTGGAAAGACGTTAACAGC

GTCCAGTTCTCCATTCTGAATAACCCGGTCGATACCGAGTTTATCAACAAGTTCCTTG

AATTCAGCAATCGCGTTTATGAGGCCCTGTATTACGTTCATAGCCTGCTGTATAGCTC

CATGACCTCTGATAGCAAATCGATCGAGAATAAACACCAACGTCGTCTGGTGAAAC

TGCTGCTGTAATGA

SUMO-GT large subunit DNA construct with His tag and linker:

(SEQ ID NO: 4)

ATGGGCCATCATCATCACCATCACGGCAGCCTGCAAGAAGAGAAACCGAAAGAGGG

CGTTAAGACCGAGAATGACCACATTAACCTGAAGGTCGCTGGTCAAGATGGCAGCG

TGGTGCAGTTTAAGATCAAGCGTCACACGCCGTTGAGCAAGCTGATGAAGGCTTACT

GCGAGCGTCAGGGTCTGAGCATGCGTCAGATCCGCTTTCGTTTCGATGGCCAGCCGA

TCAATGAGACTGACACCCCAGCGCAACTGGAGATGGAAGATGAAGATACCATCGAC

GTCTTTCAGCAACAGACCGGTGGTATGGATGCTAACGTCGTTAGCAGCAGCACCATT

GCGACTTACATTGATGCACTGGCCAAAAACGCATCTGAGCTTGAGCAGCGCAGCAC

CGCCTACGAGATCAATAACGAATTGGAGCTGGTTTTCATTAAACCGCCGCTGATCAC

GCTGACGAACGTCGTGAACATTAGCACGATTCAAGAGAGCTTTATTCGTTTCACCGT

TACCAATAAAGAAGGCGTGAAGATCCGTACCAAGATTCCGCTGAGCAAAGTGCATG

GTCTGGACGTGAAAAATGTGCAGCTGGTTGATGCGATCGATAACATCGTGTGGGAG

AAGAAATCTTTGGTCACGGAAAATCGTCTGCACAAGGAATGTCTGCTGCGTCTGTCA

ACCGAAGAACGCCACATCTTCCTGGACTACAAGAAGTATGGTTCCAGCATCCGTCTG

GAACTGGTGAACCTGATTCAGGCAAAGACCAAGAACTTCACCATTGACTTCAAACT

GAAGTATTTCCTGGGCTCTGGTGCACAGAGCAAATCCAGCTTGTTGCACGCGATTAA

CCATCCGAAGAGCCGTCCGAATACGAGCCTGGAGATCGAATTCACGCCGCGTGATA

ACGAAACCGTTCCGTACGATGAGCTGATTAAAGAACTGACGACGTTGAGCCGCCAC

-continued

```
ATCTTTATGGCCAGCCCGGAAAACGTGATCCTTAGCCCGCCTATCAATGCGCCGATT

AAAACCTTTATGTTACCGAAACAAGACATTGTGGGTCTGGACCTGGAAAACCTGTAC

GCGGTCACCAAAACGGACGGCATTCCGATCACGATTCGTGTTACCAGCAATGGTCTG

TACTGCTATTTCACTCATTTGGGCTATATCATTCGTTATCCGGTGAAACGCATCATTG

ATTCTGAGGTTGTCGTTTTCGGCGAAGCAGTCAAGGACAAGAATTGGACTGTGTACC

TGATCAAATTGATTGAACCGGTTAACGCCATCAATGACCGCCTGGAAGAGTCGAAA

TATGTTGAAAGCAAACTGGTGGATATTTGTGATCGTATCGTGTTCAAGAGCAAGAAA

TATGAAGGCCCGTTCACCACGACCAGCGAAGTTGTTGACATGCTGAGCACCTATCTG

CCGAAACAACCTGAGGGTGTGATTCTGTTTTACTCCAAGGGTCCGAAGAGCAACATT

GATTTCAAAATCAAGAAAGAGAATACCATTGATCAGACCGCCAACGTTGTGTTCCGC

TATATGTCCAGCGAGCCTATCATTTTCGGTGAGTCGAGCATCTTTGTTGAATACAAA

AAGTTTAGCAACGATAAGGGTTTTCCGAAAGAATACGGTTCCGGTAAGATTGTGTTG

TACAACGGCGTCAATTATCTGAACAACATCTACTGTCTGGAGTACATCAATACCCAT

AACGAAGTTGGCATTAAGTCTGTTGTCGTCCCGATCAAATTCATCGCGGAGTTCCTG

GTTAACGGTGAGATTCTGAAGCCGCGTATTGATAAAACTATGAAATACATTAACTCC

GAAGATTACTACGGTAATCAGCATAACATCATCGTCGAGCACTTGCGTGATCAAAGC

ATTAAGATCGGTGACATCTTTAACGAAGATAAGCTGAGCGATGTAGGCCACCAGTA

TGCGAACAATGACAAATTTCGCCTGAATCCGGAAGTCAGCTACTTTACGAATAAGCG

CACCCGTGGTCCACTGGGTATCCTGAGCAATTATGTTAAAACCCTGTTGATTTCCAT

GTACTGCTCCAAAACGTTCCTGGACGACAGCAACAAGCGCAAAGTTCTGGCGATCG

ACTTCGGTAATGGTGCCGATCTGGAGAAGTACTTTTATGGTGAGATCGCATTGCTGG

TTGCTACCGACCCGGATGCAGATGCGATCGCCCGTGGCAACGAGCGTTACAATAAG

CTGAATAGCGGTATCAAGACCAAATACTACAAATTCGACTATATTCAAGAGACGAT

CCGCTCGGACACCTTTGTATCCAGCGTGCGTGAGGTGTTTTACTTCGGTAAATTCAA

CATCATTGACTGGCAATTCGCCATTCACTATAGCTTTCACCCACGCCACTATGCGAC

GGTCATGAACAACCTGTCTGAGCTGACCGCGAGCGGCGGTAAAGTTCTGATCACCA

CGATGGACGGTGACAAGCTGTCTAAACTGACCGACAAAAAGACCTTCATTATTCAC

AAAAATCTCCCGTCGAGCGAGAATTACATGTCCGTCGAAAAGATTGCGGACGACCG

TATTGTTGTCTACAACCCGAGCACTATGTCGACCCCAATGACCGAGTATATCATCAA

AAAGAATGACATTGTGCGTGTCTTTAATGAATACGGTTTTGTGCTGGTCGACAACGT

CGATTTTGCGACCATCATCGAGAGAAGCAAGAAATTCATTAATGGCGCTTCTACGAT

GGAAGATCGCCCGAGCACGCGTAACTTCTTTGAGCTGAATCGTGGCGCGATTAAGTG

CGAGGGCCTGGACGTCGAGGATCTGCTGTCGTATTACGTGGTTTATGTGTTTAGCAA

ACGTTAATGA
```

Small ubiquitin-like modifier (SUMO) protein:

(SEQ ID NO: 1)

```
EEKPKEGVKTENDHINLKVAGQDGSVVQFKIKRHTPLSKLMKAYCERQGLSMRQIRFRF

DGQPINETDTPAQLEMEDEDTIDVFQQQTGG
```

Guanylyl transferase (GT) large subunit protein:

(SEQ ID NO: 6)

```
MDANVVSSSTIATYIDALAKNASELEQRSTAYEINNELELVFIKPPLITLTNVVNISTIQES

FIRFTVTNKEGVKIRTKIPLSKVHGLDVKNVQLVDAIDNIVWEKKSLVTENRLHKECLLR
```

-continued

```
LSTEERHIFLDYKKYGSSIRLELVNLIQAKTKNFTIDFKLKYFLGSGAQSKSSLLHAINHP

KSRPNTSLEIEFTPRDNETVPYDELIKELTTLSRHIFMASPENVILSPPINAPIKTFMLPKQD

IVGLDLENLYAVTKTDGIPITIRVTSNGLYCYFTHLGYIIRYPVKRIIDSEVVVFGEAVKDK

NWTVYLIKLIEPVNAINDRLEESKYVESKLVDICDRIVFKSKKYEGPFTTTSEVVDMLST

YLPKQPEGVILFYSKGPKSNIDFKIKKENTIDQTANVVFRYMSSEPIIFGESSIFVEYKKFS

NDKGFPKEYGSGKIVLYNGVNYLNNIYCLEYINTHNEVGIKSVVVPIKFIAEFLVNGEILK

PRIDKTMKYINSEDYYGNQHNIIVEHLRDQSIKIGDIFNEDKLSDVGHQYANNDKFRLNP

EVSYFTNKRTRGPLGILSNYVKTLLISMYCSKTFLDDSNKRKVLAIDFGNGADLEKYFY

GEIALLVATDPDADAIARGNERYNKLNSGIKTKYYKFDYIQETIRSDTFVSSVREVFYFG

KFNIIDWQFAIHYSFHPRHYATVMNNLSELTASGGKVLITTMDGDKLSKLTDKKTFIIHK

NLPSSENYMSVEKIADDRIVVYNPSTMSTPMTEYIIKKNDIVRVFNEYGFVLVDNVDFAT

IIERSKKFINGASTMEDRPSTRNFFELNRGAIKCEGLDVEDLLSYYVVVYVFSKR
```

Guanylyl transferase (GT) small subunit protein:

(SEQ ID NO: 7)
```
MDEIVKNIREGTHVLLPFYETLPELNLSLGKSPLPSLEYGANYFLQISRVNDLNRMPTDM

LKLFTHDIMLPESDLDKVYEILKINSVKYYGRSTKADAVVADLSARNKLFKRERDAIKS

NNHLTENNLYISDYKMLTFDVFRPLFDFVNEKYCIIKLPTLFGRGVIDTMRIYCSLFKNV

RLLKCVSDSWLKDSAIMVASDVCKKNLDLFMSHVKSVTKSSSWKDVNSVQFSILNNPV

DTEFINKFLEFSNRVYEALYYVHSLLYSSMTSDSKSIENKHQRRLVKLLL
```

SUMO-GT large subunit protein with His tag and linker:

(SEQ ID NO: 8)
```
MGHHHHHHGSLQEEKPKEGVKTENDHINLKVAGQDGSVVQFKIKRHTPLSKLMKAYC

ERQGLSMRQIRFRFDGQPINETDTPAQLEMEDEDTIDVFQQQTGGMDANVVSSSTIATYI

DALAKNASELEQRSTAYEINNELELVFIKPPLITLTNVVNISTIQESFIRFTVTNKEGVKIRT

KIPLSKVHGLDVKNVQLVDAIDNIVWEKKSLVTENRLHKECLLRLSTEERHIFLDYKKY

GSSIRLELVNLIQAKTKNFTIDFKLKYFLGSGAQSKSSLLHAINHPKSRPNTSLEIEFTPRD

NETVPYDELIKELTTLSRHIFMASPENVILSPPINAPIKTFMLPKQDIVGLDLENLYAVTKT

DGIPITIRVTSNGLYCYFTHLGYIIRYPVKRIIDSEVVVFGEAVKDKNWTVYLIKLIEPVNA

INDRLEESKYVESKLVDICDRIVFKSKKYEGPFTTTSEVVDMLSTYLPKQPEGVILFYSKG

PKSNIDFKIKKENTIDQTANVVFRYMSSEPIIFGESSIFVEYKKFSNDKGFPKEYGSGKIVL

YNGVNYLNNIYCLEYINTHNEVGIKSVVVPIKFIAEFLVNGEILKPRIDKTMKYINSEDYY

GNQHNIIVEHLRDQSIKIGDIFNEDKLSDVGHQYANNDKFRLNPEVSYFTNKRTRGPLGI

LSNYVKTLLISMYCSKTFLDDSNKRKVLAIDFGNGADLEKYFYGEIALLVATDPDADAI

ARGNERYNKLNSGIKTKYYKFDYIQETIRSDTFVSSVREVFYFGKFNIIDWQFAIHYSFHP

RHYATVMNNLSELTASGGKVLITTMDGDKLSKLTDKKTFIIHKNLPSSENYMSVEKIAD

DRIVVYNPSTMSTPMTEYIIKKNDIVRVFNEYGFVLVDNVDFATIIERSKKFINGASTMED

RPSTRNFFELNRGAIKCEGLDVEDLLSYYVVVYVFSKR
```

Example 2: Production of SUMO-GT Protein

Shake Flask

Production of SUMO-GT fusion protein can be performed according to standard methods and procedures. For example, to test and compare expression of the GT and SUMO-GT fusion proteins, a single colony of the *E. coli* Rosetta strain (Novagen) containing each of the SUMO-eGFP plasmids was inoculated into 5 ml of Luria-Bertani (LB) media containing 100 ug/ml Kanamycin and 30 µg/ml chloramphenicol. This strain is derived from the lambda DE3 lysogen strain and carries a chromosomal copy of the IPTG-inducible T7 RNA polymerase along with tRNAs on a pACYC-based plasmid. The cells were grown at 37° C. overnight with shaking at 250 rpm. The next morning the overnight culture was transferred into 100 ml fresh medium to permit exponential growth. When the OD600 value reached −0.6-0.7, protein expression was induced by addition of 1 mM IPTG (isopropyl-β-D-thiogalactopyrano-
side), followed by prolonged cultivation at either 37° C. for
3 hours or 20° C. overnight (about 15 hours).

After the *E. coli* cells were harvested from LB medium
(100 ml) by centrifugation (8,000×g for 10 min at 4° C.), the
cell pellets were suspended in 6 ml of lysis buffer (PBS
containing 300 mM NaCl, 10 mM imidazole, Detergent
0.1% TRITON™ X-100 and 1 mM PMSF, pH 8.0). The
cells were lysed by sonication (at 50% output for 5×30
second pulses). The sonication was conducted with the tube
jacketed in wet ice and 1 min intervals between the pulse
cycles to prevent heating. After the lysates were incubated
with DNase and RNase (each at 40 µg/ml) for 15 min to
digest nucleic acids, they were centrifuged at 20,000 g for 30
min at 4° C., and the supernatant (soluble protein fractions)
was collected. The pellets was washed once with 6 ml of the
lysis buffer to further extract the soluble fraction; the wash
(6 ml) was combined with previous extract (6 ml) to make
final volume of 12 ml for the soluble protein sample.

Insoluble protein samples were prepared from *E. coli*
inclusion bodies. Briefly, after the extract containing soluble
proteins were removed, the pellets containing inclusion
bodies were suspended in the denaturing solubilization
buffer (Novagen) that contained 50 mM CAPS (pH 11.0),
0.3% N-laurylsarcosine, and 1 mM DTT and incubated for
20 min at room temperature with shaking. The extract
(insoluble protein fraction) was obtained by high-speed
centrifugation (80,000×g for 20 min at 4° C.).

For detection of expressed proteins using SDS-PAGE, 5
µl of the samples prepared above were mixed with 3 µl of
SDSPAGE sample buffer containing SDS and β-mercaptoethanol and were heated at 95° C. for 5 min to facilitate
denaturation and reduction of proteins. Proteins were visu-
alized using 15% SDS-polyacrylamide gels with Tris-Gly-
cine running buffer and Coomassie blue staining.

Fermentation

The substantial increase in the solubility of the final
SUMO-GT complexed enzyme was also reproduced by
fermentation. Fermentation was performed according to
standard methods and procedures. For example, fermenta-
tion methods for production of SUMO-GT fusion protein
comprised cell lysis, Immobilized Metal Affinity Chroma-
tography (IMAC), Cation Exchange Chromatography,
Anion Exchange Chromatography, and Tangential Flow
Filtration (TFF) formulation. Quality testing of the SUMO-
GT fusion protein that resulted from fermentation comprised
Reducing SDS PAGE to determine purity and identity,
Reverse-Phase HPLC to determine purity, A280 measure-
ment of concentration and Limulus amebocyte lysate (LAL)
assay to test for endotoxin.

As shown in FIG. 2, the yield of soluble SUMO-GT
protein produced by fermentation is comparable to that of
GT protein produced via the shake flask method.

Equivalents

Those skilled in the art will recognize, or be able to
ascertain using no more than routine experimentation, many
equivalents to the specific embodiments of the invention
described herein. The scope of the present invention is not
intended to be limited to the above Description, but rather is
as set forth in the following claims:

We claim:

1. A method of producing a capped RNA or RNA analog oligonucleotide, comprising transferring and methylating a guanylyl molecule to the 5' end of the RNA or RNA analog oligonucleotide using a guanylyl transferase, wherein the guanylyl transferase comprises i) a fusion protein comprising a small ubiquitin-like molecule (SUMO) protein covalently linked to guanylyl transferase large subunit, wherein the SUMO protein comprises SEQ ID NO: 1 and the guanylyl transferase large subunit comprises SEQ ID NO: 6, and ii) a guanylyl transferase small subunit comprising SEQ ID NO: 7, thereby producing a capped RNA or RNA analog oligonucleotide.

2. The method of claim 1, wherein the fusion protein comprises, from the N-terminal to the C-terminal direction, SEQ ID NO: 1 fused to SEQ ID NO: 6.

3. The method of claim 1, wherein the guanylyl transferase has comparable phosphatase activity, guanylyl transferase activity and methylation activity relative to a wild-type guanylyl transferase protein.

4. The method of claim 1, wherein the RNA or RNA analog oligonucleotide is mRNA synthesized by in vitro transcription.

* * * * *

SEQUENCE LISTING

```
Sequence total quantity: 8
SEQ ID NO: 1              moltype = AA   length = 90
FEATURE                  Location/Qualifiers
REGION                   1..90
                         note = chemically synthesized polypeptide
source                   1..90
                         mol_type = protein
                         organism = synthetic construct
SEQUENCE: 1
EEKPKEGVKT ENDHINLKVA GQDGSVVQFK IKRHTPLSKL MKAYCERQGL SMRQIRFRFD   60
GQPINETDTP AQLEMEDEDT IDVFQQQTGG                                    90

SEQ ID NO: 2              moltype = DNA   length = 2588
FEATURE                  Location/Qualifiers
misc_feature             1..2588
                         note = chemically synthesized oligonucleotide
source                   1..2588
                         mol_type = other DNA
                         organism = synthetic construct
SEQUENCE: 2
agatggaaga tgaagatacc atcgacgtct ttcagcaaca gaccggtggt atggatgcta   60
acgtcgttag cagcagcacc attgcgactt acattgatgc actggccaaa aacgcatctg  120
agcttgagca gcgcagcacc gcctacgaga tcaataacga attggagctg gttttcatta  180
aaccgccgct gatcacgctg acgaacgtcg tgaacattag cacgattcaa gagagcttta  240
ttcgtttcac cgttaccaat aaagaaggcg tgaagatccg taccaagatt ccgctgagca  300
aagtgcatgg tctggacgtg aaaaatgtgc agctggttga tgcgatcgat aacatcgtgt  360
gggagaagaa atctttggtc acggaaaatc gtctgcacaa ggaatgtctg ctgcgtctgt  420
caaccgaaga acgccacatc ttcctggact acaagaagta tggttccagc atccgtctgg  480
aactggtgaa cctgattcag gcaaagacca agaacttcac cattgacttc aaactgaagt  540
atttcctggg ctctggtgca cagagcaaat ccagcttgtt gcacgcgatt aaccatccga  600
agagccgtcc gaatacgagc ctggagatcg aattcacgcc gcgtgataac gaaaccgttc  660
cgtacgatga gctgattaaa gaactgacga cgttgagccg ccacatcttt atggccagcc  720
cggaaaacgt gatccttagc ccgcctatca atgcgccgat taaaaccttt atgttaccga  780
aacaagacat tgtgggtctg gacctggaaa acctgtacgc ggtcaccaaa acggacggca  840
ttccgatcac gattcgtgtt accagcaatg gtctgtactg ctatttcact catttgggct  900
atatcattcg ttatccggtg aaacgcatca ttgattctga ggttgtcgtt ttcggcgaag  960
cagtcaagga caagaattgg actgtgtacc tgatcaaatt gattgaaccg gttaacgcca 1020
tcaatgaccg cctggaagag tcgaaatatg ttgaaagcaa actggtggat atttgtgatc 1080
```

```
gtatcgtgtt caagagcaag aaatatgaag gcccgttcac cacgaccagc gaagttgttg   1140
acatgctgag cacctatctg ccgaaacaac ctgagggtgt gattctgttt tactccaagg   1200
gtccgaagag caacattgat ttcaaaatca agaaagagaa taccattgat cagaccgcca   1260
acgttgtgtt ccgctatatg tccagcgagc ctatcatttt cggtgagtcg agcatctttg   1320
ttgaatacaa aaagtttagc aacgataagg gttttccgaa agaatacggt tccggtaaga   1380
ttgtgttgta caacggcgtc aattatctga acaacatcta ctgtctggag tacatcaata   1440
cccataacga agttggcatt aagtctgttg tcgtcccgat caaattcatc gcggagttcc   1500
tggttaacgg tgagattctg aagccgcgta ttgataaaac tatgaaatac attaactccg   1560
aagattacta cggtaatcag cataacatca tcgtcgagca cttgcgtgat caaagcatta   1620
agatcggtga catctttaac gaagataagc tgagcgatgt aggccaccag tatgcgaaca   1680
atgacaaatt tcgcctgaat ccggaagtca gctactttac gaataagcgc acccgtggtc   1740
cactgggtat cctgagcaat tatgttaaaa ccctgttgat ttccatgtac tgctccaaaa   1800
cgttcctgga cgacagcaac aagcgcaaag ttctggcgat cgacttcggt aatggtgccg   1860
atctggagaa gtactttat ggtgagatcg cattgctggt tgctaccgac ccggatgcag   1920
atgcgatcgc ccgtggcaac gagcgttaca ataagctgaa tagcggtatc aagaccaaat   1980
actacaaatt cgactatatt caagagacga tccgctcgga caccttttgta tccagcgtgc   2040
gtgaggtgtt ttacttcggt aaattcaaca tcattgactg gcaattcgcc attcactata   2100
gctttcaccc acgccactat gcgacggtca tgaacaacct gtctgagctg accgcgagcg   2160
gcggtaaagt tctgatcacc acgatggacg gtgacaagtc gtctaaactg accgacaaaa   2220
agaccttcat tattcacaaa aatctcccgt cgagcgagaa ttacatgtcc gtcgaaagaa   2280
ttgcggacga ccgtattgtt gtctacaacc cgagcactat gtcgacccca atgaccgagt   2340
atatcatcaa aaagaatgac attgtgcgtg tctttaatga atacggtttt gtgctggtcg   2400
acaacgtcga tttgcgacc atcatcgaga gaagcaagaa attcattaat ggcgcttcta   2460
cgatggaaga tcgcccgagc acgcgtaact tctttgagct gaatcgtggc gcgattaagt   2520
gcgagggcct ggacgtcgag gatctgctgt cgtattacgg ggtttatgtg tttagcaaac   2580
gttaatga                                                            2588

SEQ ID NO: 3          moltype = DNA  length = 867
FEATURE               Location/Qualifiers
misc_feature          1..867
                      note = chemically synthesized oligonucleotide
source                1..867
                      mol_type = other DNA
                      organism = synthetic construct
SEQUENCE: 3
atggacgaaa ttgtcaagaa tatccgtgaa ggtacccacg ttttactgcc attctacgag   60
acgctgccgg aactgaacct gagcctgggt aaaagccctc tgccgagcct ggagtatggt   120
gcgaactatt ttctgcagat ttcccgtgta aacgatttga accgcatgcc gacggacatg   180
ctgaaactgt tcacccacga catcatgctg ccggaatctg atctggataa agtttacgag   240
atcttgaaaa tcaattcagt gaagtactat ggccgtagca ccaaggccga tgcggtggtc   300
gcagacctga gcgcgcgtaa caaactgttt aaacgtgaac gtgacgcaat taagagcaat   360
aaccatctga ccgagaacaa tttgtacatc agcgactaca agatgttgac ttttgacgtg   420
tttcgtccgc tgttcgactt tgttaatgag aaatactgca ttatcaagct gccgacgttg   480
tttggtcgcg gcgtcattga tacgatgcgc atttactgct ctctcttcaa gaatgtgcgc   540
ctgctgaagt gtgtctccga cagctggctg aaagatagcg ctattatggt tgcgagcgac   600
gtgtgtaaaa agaacctgga tctgttcatg agccacgtga gagcgttac caaaagcagc   660
agctggaaag acgttaacag cgtccagttc tccattctga ataaccggt cgataccgag   720
tttatcaaca agttccttga attcagcaat cgcgtttatg aggccctgta ttacgttcat   780
agcctgctgt atagctccat gacctctgat agcaaatcga tcgagaataa acaccaacgt   840
cgtctggtga aactgctgct gtaatga                                        867

SEQ ID NO: 4          moltype = DNA  length = 2844
FEATURE               Location/Qualifiers
misc_feature          1..2844
                      note = chemically synthesized oligonucleotide
source                1..2844
                      mol_type = other DNA
                      organism = synthetic construct
SEQUENCE: 4
atgggccatc atcatcacca tcacggcagc ctgcaagaag agaaaccgaa agagggcgtt   60
aagaccgaga atgaccacat taacctgaag gtcgctggtc aagatggcag cgtggtgcag   120
tttaagatca agcgtcacac gccgttgagc aagctgatga aggcttactg cgagcgtcag   180
ggtctgagca tgcgtcagat ccgctttcgt ttcgatggcc agccgatcaa tgagactgac   240
acccccagcgc aactggagat ggaagataaa gatactatcg acgtctttca gcaacagacc   300
ggtggtatgg atgctaacgt cgttagcagc agcaccattg cgacttacat tgatgcactg   360
gccaaaaacg catctgagct tgagcagcgc agcaccgcct acgagatcaa taacgaattg   420
gagctggttt tcattaaacc gccgctgatc acgctgacga acgtcgtgaa cattagcacg   480
attcaagaga gctttattcg tttcaccgtt accaataaag aaggcgtgaa gatccgtacc   540
aagattccgc tgagcaaagt gcatggtctg gacgtgaaaa atgtgcagct ggttgatgcg   600
atcgataaca tcgtgtggga agaaaatct ttggtcacgg aaaatcgtct gcacaaggaa   660
tgtctgctgc gtctgtcaac cgaagaacgc cacatcttcc tggactacaa gaagtatggt   720
tccagcatcc gtctggaact ggtgaacctg attcaggcaa agaccaagaa cttcaccatt   780
gacttcaaac tgaagtattt cctgggctct ggtgcacaga gcaaatccag cttgttgcac   840
gcgattaacc atccgaagag ccgtccgaat acgagcctgg agatcgaatt cacgccgcgt   900
gataacgaaa ccgttccgta cgatgagctg attaaagaac tgacgacgtt gagccgccac   960
atctttatgg ccagcccgga aaacgtgatc cttagcccgc ctatcaatgc gccgattaaa   1020
acctttatgt taccgaaaca agacattgtg ggtctggacc tggaaaacct gtacgcggtc   1080
accaaaacgg acggcattcc gatcacgatt cgtgttacca gcaatggtct gtactgctat   1140
ttcactcatt tgggctatat cattcgttat ccggtgaaac gcatcattga ttctgaggtt   1200
```

-continued

```
gtcgttttcg gcgaagcagt caaggacaag aattggactg tgtacctgat caaattgatt   1260
gaaccggtta acgccatcaa tgaccgcctg gaagagtcga aatatgttga aagcaaactg   1320
gtggatattt gtgatcgtat cgtgttcaag agcaagaaat atgaaggccc gttcaccacg   1380
accagcgaag ttgttgacat gctgagcacc tatctgccga acaacctga gggtgtgatt    1440
ctgtttact ccaagggtcc gaagagcaac attgatttca aaatcaagaa agagaatacc    1500
attgatcaga ccgccaacgt tgtgttccgc tatatgtcca gcgagcctat cattttcggt   1560
gagtcgagca tctttgttga atacaaaaag tttagcaacg ataagggttt tccgaaagaa   1620
tacggttccg gtaagattgt gttgtacaac ggcgtcaatt atctgaacaa catctactgt   1680
ctggagtaca tcaataccca taacgaagtt ggcattaagt ctgttgtcgt cccgatcaaa   1740
ttcatcgcgg agttcctggt taacggtgag attctgaagc cgcgtattga taaaactatg   1800
aaatacatta actccgaaga ttactacggt aatcagcata acatcatcgt cgagcacttg   1860
cgtgatcaaa gcattaagat cggtgacatc tttaacgaag ataagctgag cgatgtaggc   1920
caccagtatg cgaacaatga caaatttcgc ctgaatccgg aagtcagcta ctttacgaat   1980
aagcgcaccc gtggtccact gggtatcctg agcaattatg ttaaaaccct gttgatttcc   2040
atgtactgct ccaaaacgtt cctggacgac agcaacaagc gcaaagttct ggcgatcgac   2100
ttcggtaatg gtgccgatct ggagaagtac ttttatggtg agatcgcatt gctggttgct   2160
accgacccgg atgcagatgc gatcgcccgt ggcaacgagc gttacaataa gctgaatagc   2220
ggtatcaaga ccaaatacta caaattcgac tatattcaag agcgatccg ctcggacacc    2280
tttgtatcca gcgtgcgtga ggtgtttac ttcggtaaat tcaacatcat tgactggcaa    2340
ttcgccattc actatagctt tcacccacgc cactatgcga cggtcatgaa caacctgtct   2400
gagctgaccg cgagcggcgg taaagttctg atcaccacga tggacggtga caagctgtct   2460
aaactgaccg acaaaaagac cttcattatt cacaaaaatc tcccgtcgag cgagaattac   2520
atgtccgtcg aaaagattgc ggacgaccgt attgttgtct acaacccgag cactatgtcg   2580
accccaatga ccgagtatat catcaaaaag aatgacattg tgcgtgtctt taatgaatac   2640
ggttttgtgc tggtcgacaa cgtcgatttt gcgaccatca tcgagagaag caagaaattc   2700
attaatggcg cttctacgat ggaagatcgc ccgagcacgc gtaacttctt tgagctgaat   2760
cgtggcgcga ttaagtgcga gggcctggac gtcgaggatc tgctgtcgta ttacgtggtt   2820
tatgtgtta gcaaacgtta atga                                           2844
```

```
SEQ ID NO: 5            moltype = DNA  length = 220
FEATURE                 Location/Qualifiers
misc_feature            1..220
                        note = chemically synthesized oligonucleotide
source                  1..220
                        mol_type = other DNA
                        organism = synthetic construct
SEQUENCE: 5
gaagagaaac cgaaagaggg cgttaagacc gagaatgacc acattaacct gaaggtcgct   60
ggtcaagatg gcagcgtggt gcagtttaag atcaagcgtc acacgccgtt gagcaagctg   120
atgaaggctt actgcgagcg tcagggtctg agcatgcgtc agatccgctt tcgtttcgat   180
ggccagccga tcaatgagac tgacaccccca gcgcaactgg                        220
```

```
SEQ ID NO: 6            moltype = AA  length = 844
FEATURE                 Location/Qualifiers
REGION                  1..844
                        note = chemically synthesized polypeptide
source                  1..844
                        mol_type = protein
                        organism = synthetic construct
SEQUENCE: 6
MDANVVSSST IATYIDALAK NASELEQRST AYEINNELEL VFIKPPLITL TNVVNISTIQ   60
ESFIRFTVTN KEGVKIRTKI PLSKVHGLDV KNVQLVDAID NIVWEKKSLV TENRLHKECL   120
LRLSTEERHI FLDYKKYGSS IRLELVNLIQ AKTKNFTIDF KLKYFLGSGA QSKSSLLHAI   180
NHPKSRPNTS LEIEFTPRDN ETVPYDELIK ELTTLSRHIF MASPENVILS PPINAPIKTF   240
MLPKQDIVGL DLENLYAVTK TDGIPITIRV TSNGLYCYFT HLGYIIRYPV KRIIDSEVVV   300
FGEAVKDKNW TVYLIKLIEP VNAINDRLEE SKYVESKLVD ICDRIVFKSK KYEGPFTTTS   360
EVVDMLSTYL PKQPEGVILF YSKGPKSNID FKIKKENTID QTANVVFRYM SSEPIIFGES   420
SIFVEYKKFS NDKGFPKEYG SGKIVLYNGV NYLNNIYCLE YINTHNEVGI KSVVVPIKFI   480
AEFLVNGEIL KPRIDKTMKY INSEDYYGNQ HNIIVEHLRD QSIKIGDIFN EDKLSDVGHQ   540
YANNDKFRLN PEVSYFTNKR TRGPLGILSN YVKTLLISMY CSKTFLDDSN KRKVLAIDFG   600
NGADLEKYFY GEIALLVATD PDADAIARGN ERYNKLNSGI KTKYYKFDYI QETIRSDTFV   660
SSVREVFYFG KFNIIDWQFA IHYSFHPRHY ATVMNNLSEL TASGGKVLIT TMDGDKLSKL   720
TDKKTFIIHK NLPSSENYMS VEKIADDRIV VYNPSTMSTP MTEYIIKKND IVRVFNEYGF   780
VLVDNVDFAT IIERSKKFIN GASTMEDRPS TRNFFELNRG AIKCEGLDVE DLLSYYVVYV   840
FSKR                                                                844
```

```
SEQ ID NO: 7            moltype = AA  length = 287
FEATURE                 Location/Qualifiers
REGION                  1..287
                        note = chemically synthesized polypeptide
source                  1..287
                        mol_type = protein
                        organism = synthetic construct
SEQUENCE: 7
MDEIVKNIRE GTHVLLPFYE TLPELNLSLG KSPLPSLEYG ANYFLQISRV NDLNRMPTDM   60
LKLFTHDIML PESDLDKVYE ILKINSVKYY GRSTKADAVV ADLSARNKLF KRERDAIKSN   120
NHLTENNLYI SDYKMLTFDV FRPLFDFVNE KYCIIKLPTL FGRGVIDTMR IYCSLFKNVR   180
LLKCVSDSWL KDSAIMVASD VCKKNLDLFM SHVKSVTKSS SWKDVNSVQF SILNNPVDTE   240
FINKFLEFSN RVYEALYYVH SLLYSSMTSD SKSIENKHQR RLVKLLL               287
```

-continued

```
SEQ ID NO: 8              moltype = AA   length = 946
FEATURE                  Location/Qualifiers
REGION                   1..946
                         note = chemically synthesized polypeptide
source                   1..946
                         mol_type = protein
                         organism = synthetic construct
SEQUENCE: 8
MGHHHHHHGS LQEEKPKEGV KTENDHINLK VAGQDGSVVQ FKIKRHTPLS KLMKAYCERQ   60
GLSMRQIRFR FDGQPINETD TPAQLEMEDE DTIDVFQQQT GGMDANVVSS STIATYIDAL  120
AKNASELEQR STAYEINNEL ELVFIKPPLI TLTNVVNIST IQESFIRFTV TNKEGVKIRT  180
KIPLSKVHGL DVKNVQLVDA IDNIVWEKKS LVTENRLHKE CLLRLSTEER HIFLDYKKYG  240
SSIRLELVNL IQAKTKNFTI DFKLKYFLGS GAQSKSSLLH AINHPKSRPN TSLEIEFTPR  300
DNETVPYDEL IKELTTLSRH IFMASPENVI LSPPINAPIK TFMLPKQDIV GLDLENLYAV  360
TKTDGIPITI RVTSNGLYCY FTHLGYIIRY PVKRIIDSEV VVFGEAVKDK NWTVYLIKLI  420
EPVNAINDRL EESKYVESKL VDICDRIVFK SKKYEGPFTT TSEVVDMLST YLPKQPEGVI  480
LFYSKGPKSN IDFKIKKENT IDQTANVVFR YMSSEPIIFG ESSIFVEYKK FSNDKGFPKE  540
YGSGKIVLYN GVNYLNNIYC LEYINTHNEV GIKSVVVPIK FIAEFLVNGE ILKPRIDKTM  600
KYINSEDYYG NQHNIIVEHL RDQSIKIGDI FNEDKLSDVG HQYANNDKFR LNPEVSYFTN  660
KRTRGPLGIL SNYVKTLLIS MYCSKTFLDD SNKRKVLAID FGNGADLEKY FYGEIALLVA  720
TDPDADAIAR GNERYNKLNS GIKTKYYKFD YIQETIRSDT FVSSVREVFY FGKFNIIDWQ  780
FAIHYSFHPR HYATVMNNLS ELTASGGKVL ITTMDGDKLS KLTDKKTFII HKNLPSSENY  840
MSVEKIADDR IVVYNPSTMS TPMTEYIIKK NDIVRVFNEY GFVLVDNVDF ATIIERSKKF  900
INGASTMEDR PSTRNFFELN RGAIKCEGLD VEDLLSYYVV YVFSKR             946
```